United States Patent
Zhang et al.

(10) Patent No.: US 11,634,770 B2
(45) Date of Patent: Apr. 25, 2023

(54) NICKING AND EXTENSION AMPLIFICATION REACTION (NEAR) OF RESPIRATORY SYNCYTIAL VIRUS SPECIES

(71) Applicant: IONIAN TECHNOLOGIES, LLC, San Diego, CA (US)

(72) Inventors: Honghua Zhang, San Diego, CA (US); Richard Roth, San Diego, CA (US)

(73) Assignee: IONIAN TECHNOLOGIES, LLC, San Diego, CA (US)

( * ) Notice: Subject to any disclaimer, the term of this patent is extended or adjusted under 35 U.S.C. 154(b) by 529 days.

(21) Appl. No.: 16/118,081

(22) Filed: Aug. 30, 2018

(65) Prior Publication Data

US 2019/0194747 A1    Jun. 27, 2019

Related U.S. Application Data

(60) Provisional application No. 62/552,546, filed on Aug. 31, 2017.

(51) Int. Cl.
| | |
|---|---|
| C12Q 1/6876 | (2018.01) |
| C12Q 1/70 | (2006.01) |
| C12Q 1/6806 | (2018.01) |
| C12Q 1/686 | (2018.01) |

(52) U.S. Cl.
CPC ........... *C12Q 1/6876* (2013.01); *C12Q 1/686* (2013.01); *C12Q 1/6806* (2013.01); *C12Q 1/701* (2013.01); *C12N 2310/11* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 6,881,835 | B2 | 4/2005 | Bai |
| 7,270,981 | B2 | 9/2007 | Armes |
| 7,399,590 | B2 | 7/2008 | Piepenburg |
| 7,435,561 | B2 | 10/2008 | Piepenburg |
| 7,666,598 | B2 | 2/2010 | Piepenburg |
| 8,071,308 | B2 | 12/2011 | Piepenburg |
| 9,096,897 | B2 | 8/2015 | Shaffer |
| 9,617,586 | B2 | 4/2017 | Maples |
| 9,689,031 | B2 | 6/2017 | Maples |
| 10,851,406 | B2 * | 12/2020 | Maples ............... C12Q 1/6844 |
| 2006/0287267 | A1 | 12/2006 | Vaish |
| 2007/0054296 | A1 | 3/2007 | Piepenburg et al. |
| 2009/0017453 | A1 * | 1/2009 | Maples ............... C12Q 1/686 |
| | | | 435/6.12 |
| 2017/0183714 | A1 | 6/2017 | Shen |
| 2018/0023130 | A1 * | 1/2018 | Maples ............... C12Q 1/6844 |
| | | | 435/6.12 |

FOREIGN PATENT DOCUMENTS

WO    2010141940 A1    12/2010

OTHER PUBLICATIONS

Collins, Respiratory Syncytial Virus: Virology, Reverse Genetics, and Pathogenesis of Disease, Curr Top Microbiol Immuno, 372: 3-38, 2013. (Year: 2013).*
New England BioLabs, Restriction Endonucleases, Products, Nt.CviPII, 2021. (Year: 2021).*
Lowe, A computer program for selection of oligonucleotide primers for polymerase chain reactions, Nucleic Acids Research, 18(7): 1757-1761, 1996). (Year: 1990).*
Gen Bank Accession No. U39662.1, 2006. (Year: 2006).*
FDA CDRH, 501(k) report K161375, "To establish substantial equivalance to a predicate device amd to obtain clearance for a new assay: the Alere i RSV test." 22 pages. accessed Oct. 21, 2018, at <URL:https://www.accessdata.fda.gov/cdrh_docs/reviews/K161375.pdf.
Hall et al.,"Respiratory syncytial virus-associated hospitalizations among children less than 24 months of age." Pediatrics. Aug. 2013;132(2):e341-8.
The International Search Report, for the corresponding PCT Application No. PCT/US2018/048903, dated Jan. 29, 2019, 16 pages.
Langley et al., "Epidemiology and prevention of respiratory syncytial virus infections among infants and young children." Pediatr Infect Dis J. Jun. 2011;30(6):510-7.
Stockman et al., "Respiratory syncytial virus-associated hospitalizations among infants and young children in the United States, 1997-2006." Pediatr Infect Dis J. Jan. 2012;31(1):5-9.
GenBank Accession No. NC_001803.1, retrieved Nov. 13, 2018, 8 pages.
GenBank Accession No. N2 KF893260.1., retrieved Nov. 13, 2018, 7 pages.
Anonymous: "To establish substantial equivalence to a predicate device and to obtain clearance for a new assay: the Alere i RSV Test", FDA CURH, 501 (k) report K161375, Aug. 18, 2016 (Aug. 18, 2016), pp. 1-21, XP055578697, Retrieved from the Internet: URL:https://www.accessdata.fda.gov/cdrh_docs/reviews/K161375.pdf [retrieved on Feb. 2, 2022].
Extended European Search Report for EP 18849601.2, dated Apr. 30, 2021, 11 pages.

\* cited by examiner

*Primary Examiner* — Angela M. Bertagna
*Assistant Examiner* — Carolyn L Greene
(74) *Attorney, Agent, or Firm* — Casimir Jones S.C.; Thomas A. Isenbarger

(57) ABSTRACT

This invention relates to methods and compositions for detecting the presence or absence of a Respiratory Syncytial Virus target nucleic acid in a biological sample using isothermal nucleic acid amplification.

17 Claims, 20 Drawing Sheets

Specification includes a Sequence Listing.

NICKING AND EXTENSION AMPLIFICATION REACTION (NEAR) OF RESPIRATORY SYNCYTIAL VIRUS SPECIES

CROSS-REFERENCE TO RELATED APPLICATION

This application claims the benefit of U.S. patent application Ser. No. 62/552,546 filed Aug. 31, 2017, which is hereby incorporated by reference in its entirety.

SEQUENCE LISTING

The text of the computer readable sequence listing filed herewith, titled "35646-US-2-ORD-SQL_ST25", created Aug. 30, 2018, having a file size of 7,436 bytes, is hereby incorporated by reference in its entirety.

TECHNICAL FIELD

This invention relates to methods and compositions for detecting the presence or absence of a target nucleic acid in a biological sample using isothermal nucleic acid amplification. More specifically, the present invention relates to detecting Respiratory Syncytial Virus target nucleic acid in a biological sample.

BACKGROUND

Certain isothermal amplification methods are able to amplify a target nucleic acid from trace levels to very high and detectable levels within a matter of minutes. Such isothermal methods, e.g., Nicking and Extension Amplification Reaction (NEAR), allow users to detect a particular nucleotide sequence in trace amounts, facilitating point-of-care testing and increasing the accessibility and speed of diagnostics.

Respiratory Syncytial Virus ("RSV") is a single-stranded enveloped RNA Paramyxovirus that has at least ten proteins and three surface proteins. RSV is the causative agent of the most common pediatric respiratory infections (e.g., bronchiolitis and pneumonia). While a majority of RSV infections affect infants under the age of one, more than 170,000 children under the age of five are hospitalized each year in the United States due to RSV (see, e.g., Stockman et al. (2012) *Pediatr. Infect. Dis. J.* 31(1): 5-9; Hall et al. (2013) *Pediatrics* 132(2): e341-348; and Langley et al. (2011) *Pediatr. Infect. Dis. J.* 30(6): 517-517). RSV infections are also seen in the elderly and in high-risk adults (i.e., immunocompromised patients). With an incubation period of 3-5 days, RSV infections typically remain undetected for several days. Symptoms associated with RSV infection include those typically associated with cold symptoms (e.g., congestion, cough and fever). These exemplary factors render early detection and diagnosis very challenging.

SUMMARY

This disclosure is based, at least in part, on the discovery that the presence or absence of RSV in a biological sample can be accurately and efficiently detected using NEAR or Recombinase Polymerase Amplification (RPA). In view of this discovery, provided herein are NEAR compositions and methods for determining (e.g., detecting) the presence or absence of RSV in a biological sample. More particularly, provided herein are NEAR compositions and methods for determining (e.g., detecting) the presence or absence of a RSV target nucleic acid such as, for example, the nonstructural gene NS2 or the RSV nucleocapsid gene N, in a biological sample. The compositions provided herein are useful for the detection of RSV nucleic acid in a biological sample, and comprise at least one pair of templates (i.e., a forward and reverse template pair), and optionally a probe, specific for RSV.

Provided herein are compositions including: i) a first forward template including a nucleic acid sequence including a recognition region at the 3' end that is complementary to the 3' end of a Respiratory Syncytial Virus (RSV) nonstructural NS2 gene antisense strand; a nicking enzyme binding site and a nicking site upstream of the recognition region; and a stabilizing region upstream of the nicking site; and ii) a first reverse template including a nucleic acid sequence including a recognition region at the 3' end that is complementary to the 3' end of a RSV nonstructural NS2 gene sense strand; a nicking enzyme binding site and a nicking site upstream of the recognition region; and a stabilizing region upstream of the nicking site; or iii) a second forward template including a nucleic acid sequence including a recognition region at the 3' end that is complementary to the 3' end of a RSV nucleocapsid gene N antisense strand; a nicking enzyme binding site and a nicking site upstream of the recognition region; and a stabilizing region upstream of the nicking site; and iv) a second reverse template including a nucleic acid sequence including a recognition region at the 3' end that is complementary to the 3' end of a RSV nucleocapsid gene N sense strand; a nicking enzyme binding site and a nicking site upstream of the recognition region; and a stabilizing region upstream of the nicking site.

In some embodiments, the recognition region at the 3' end that is complementary to the 3' end of the RSV nonstructural NS2 gene antisense strand is 8-30 nucleotides in length, and/or wherein the recognition region at the 3' end that is complementary to the 3' end of the RSV nucleocapsid gene N antisense strand is 8-30 nucleotides in length.

In some embodiments, the recognition region at the 3' end that is complementary to the 3' end of the RSV nonstructural NS2 gene sense strand is 8-30 nucleotides in length, and/or wherein the recognition region at the 3' end that is complementary to the 3' end of the RSV nucleocapsid gene N sense strand is 8-30 nucleotides in length.

In some embodiments, the composition including i) and ii) further includes a probe oligonucleotide including a nucleotide sequence complementary to the RSV nonstructural NS2 gene nucleotide sequence. In some embodiments, the composition including iii) and iv) further includes a probe oligonucleotide including a nucleotide sequence complementary to the RSV nucleocapsid gene N nucleotide sequence.

In some embodiments, the nucleic acid sequence of the first forward template includes a nucleotide sequence having at least 80%, at least 85% or at least 95% sequence identity to SEQ ID NO: 1 (CGACTCACACGAGTCGAAAACTTGATGAAAGA); and the nucleic acid sequence of the first reverse template includes a nucleotide sequence having at least 80%, at least 85% or at least 95% sequence identity to SEQ ID NO: 2: (AGACTCCACACGAGTCTAGTTGACCAGGAATG).

In some embodiments of any of the compositions described herein, the composition including i) and ii) further includes a probe oligonucleotide including a nucleotide sequence having at least 80%, at least 85% or at least 95% sequence identity to SEQ ID NO: 3 (ACCAGGAATGTAAATGTGGCCTGGT). In some embodiments, the nucleic acid sequence of the second forward template includes a nucleotide sequence having at least 80%, at least 85% or at least 95% sequence identity to SEQ ID NO: 6 (GACTCGCACACGAGTCACGTAGTACAGGAGA-TAA); the nucleic acid sequence of the second reverse template includes a nucleotide sequence having at least 80%, at least 85% or at least 95% sequence identity to SEQ ID NO 7: (GACTCCACACGGAGTCGCTTTTGCACAT-CATAA).

In some embodiments, the composition including iii) and iv) further includes a probe oligonucleotide including a nucleotide sequence having at least 80%, at least 85% or at least 95% sequence identity to SEQ ID NO: 8 (TGACA-CATCATAATTGGGAGTGTCA).

In some embodiments of any of the compositions described herein, further including one or more of a DNA polymerase, one or more nicking enzymes, dNTPs or a mixture of dNTPs and ddNTPs. In some embodiments, the DNA polymerase is selected from the group consisting of *Geobacillus bogazici* DNA polymerase, Bst (large fragment), exo-DNA Polymerase, Manta 1.0 DNA Polymerase (Enzymatics®). In some embodiments, the one or more nicking enzymes are selected from the group consisting of Nt. BspQI, Nb. BbvCi, Nb. BsmI, Nb. BsrDI, Nb. BtsI, Nt. AlwI, Nt. BbvCI, Nt. BstNBI, Nt. CviPII, Nb. Bpu10I, Nt. Bpu10I and N. BspD6I.

In some embodiments, the composition is lyophilized.

In some embodiments, the probe is conjugated to a detectable label. In some embodiments, the detectable label is selected from the group consisting of a fluorophore, an enzyme, a quencher, an enzyme inhibitor, a radioactive label, a member of a binding pair, and a combination thereof.

In some embodiments, one or more of the first forward template, the first reverse template, the second forward template or the second reverse template includes one or more modified nucleotides, spacers, or blocking groups. In some embodiments, at least one modified nucleotide includes a 2'modification. In some embodiments, at least one modified nucleotide includes a 2'—O-methyl.

Also provided herein are methods for the detection of the presence or absence of RSV in a biological sample, wherein the method includes: contacting the biological sample with a composition comprising i) a first forward template including a nucleotide sequence including a recognition region at the 3' end that is complementary to the 3' end of a RSV nonstructural NS2 gene antisense strand; a nicking enzyme binding site and a nicking site upstream of the recognition region; and a stabilizing region upstream of the nicking site; ii) a first reverse template including a nucleotide sequence including a recognition region at the 3' end that is complementary to the 3' end of RSV nonstructural NS2 gene sense strand; a nicking enzyme binding site and a nicking site upstream of the recognition region; and a stabilizing region upstream of the nicking site; iii) at least one nicking enzyme; and iv) a DNA polymerase; amplifying the target nucleotide sequence in a nucleic amplification reaction to provide an amplification product; and detecting the presence or absence of the amplification product.

In some embodiments, the at least one nicking enzyme includes a first nicking enzyme that is capable of nicking at the nicking site of the first forward template, and does not nick within the RSV nonstructural NS2 gene antisense strand, and/or a second nicking enzyme that is capable of nicking at the nicking site of the first reverse template and does not nick within the RSV nonstructural NS2 gene sense strand, wherein the first nicking enzyme and the second nicking enzyme may be the same or different. In some embodiments, the composition further includes a probe oligonucleotide including a nucleotide sequence complementary to the RSV nonstructural NS2 gene nucleotide sequence.

Also provided herein are methods for the detection of the presence or absence of RSV in a biological sample, wherein the method includes: contacting the biological sample with a composition including i) a second forward template including a nucleotide sequence including a recognition region at the 3' end that is complementary to the 3' end of a RSV nucleocapsid gene N antisense strand; a nicking enzyme binding site and a nicking site upstream of the recognition region; and a stabilizing region upstream of the nicking site, ii) a second reverse template including a nucleotide sequence including a recognition region at the 3' end that is complementary to the 3' end of a RSV nucleocapsid gene N sense strand; a nicking enzyme binding site and a nicking site upstream of the recognition region; and a stabilizing region upstream of the nicking site, iii) at least one nicking enzyme; and iv) a DNA polymerase; amplifying the target nucleotide sequence in a nucleic amplification reaction to provide an amplification product; and detecting the presence or absence of the amplification product.

In some embodiments, the at least one nicking enzyme includes a first nicking enzyme that is capable of nicking at the nicking site of the second forward template, and does not nick within the RSV nucleocapsid gene N antisense strand, and/or a second nicking enzyme that is capable of nicking at the nicking site of the second reverse template and does not nick within the nucleocapsid gene N sense strand, wherein the first nicking enzyme and the second nicking enzyme may be the same or different.

In some embodiments, the composition further includes a probe oligonucleotide including a nucleotide sequence complementary to the RSV nucleocapsid gene N nucleotide sequence.

In some embodiments, amplification is performed under essentially isothermal conditions.

In some embodiments, the nucleic acid sequence of the first forward template includes a nucleotide sequence having at least 80%, at least 85% or at least 95% sequence identity to SEQ ID NO: 1; and the nucleic acid sequence of the first reverse template includes a nucleotide sequence having at least 80%, at least 85% or at least 95% sequence identity to SEQ ID NO 2. In some embodiments, the probe oligonucleotide includes a nucleotide sequence having at least 80%, at least 85% or at least 95% sequence identity to SEQ ID NO: 3. In some embodiments, the nucleic acid sequence of the second forward template includes a nucleotide sequence having at least 80%, at least 85% or at least 95% sequence identity to SEQ ID NO: 6; and the nucleic acid sequence of the second reverse template includes a nucleotide sequence having at least 80%, at least 85% or at least 95% sequence identity to SEQ ID NO 7. In some embodiments, the probe oligonucleotide includes a nucleotide sequence having at least 80%, at least 85% or at least 95% sequence identity to SEQ ID NO: 8.

In some embodiments, the composition further includes dNTPs or a mixture of dNTPs and ddNTPs.

In some embodiments, the DNA polymerase is selected from the group consisting of *Geobacillus bogazici* DNA polymerase, Bst (large fragment), exo-DNA Polymerase, Manta 1.0 DNA Polymerase (Enzymatics®). In some embodiments, the first forward and first reverse templates the second forward and second reverse templates comprise nicking enzyme binding sites recognized by the same at least one nicking enzyme. In some embodiments, the at least one nicking enzyme is selected from the group consisting of Nt. BspQI, Nb. BbvCi, Nb. BsmI, Nb. BsrDI, Nb. BtsI, Nt. AlwI, Nt. BbvCI, Nt. BstNBI, Nt. CviPII, Nb. Bpu10I, Nt. Bpu10I and N. SBspD61.

In some embodiments, the probe is conjugated to a detectable label. In some embodiments, the detectable label is selected from the group consisting of a fluorophore, an enzyme, a quencher, an enzyme inhibitor, a radioactive label, a member of a binding pair, and a combination thereof. In some embodiments, the at least one nicking enzyme nicks downstream of the nicking enzyme binding site.

In some embodiments of any of the methods described herein, the method optionally includes extracting/isolating a nucleic acid from the biological sample prior to amplifying.

In some embodiments, the biological sample is selected from feces, swabs of the oral cavity/throat, saliva, pus, sputum, blood, and urine, or wherein the biological sample is from infected or non-infected tissues.

In some embodiments, one or more of the first forward template, the first reverse template, the second forward template or the second reverse template includes one or more modified nucleotides, spacers, or blocking groups. In some embodiments, at least one modified nucleotide includes a 2'modification. In some embodiments, at least one modified nucleotide includes a 2'—O-methyl.

Also provided herein are kits that include a template oligonucleotide selected from the group consisting of: (a) a first forward template including a nucleotide sequence having at least 80%, at least 85% or at least 95% sequence identity to SEQ ID NO: 1; and a first reverse template including a nucleotide sequence having at least 80%, at least 85% or at least 95% sequence identity to SEQ ID NO 2; or (b) a second forward template including a nucleotide sequence having at least 80%, at least 85% or at least 95% sequence identity to SEQ ID NO: 6; and a second reverse including a nucleotide sequence having at least 80%, at least 85% or at least 95% sequence identity to SEQ ID NO 7.

In some embodiments of any of the kits described herein, (a) further includes a probe oligonucleotide including a nucleotide sequence having at least 80%, at least 85% or at least 95% sequence identity to SEQ ID NO: 3. In some embodiments of any of the kits described herein, (b) further includes a probe oligonucleotide including a nucleotide sequence having at least 80%, at least 85% or at least 95% sequence identity to SEQ ID NO: 8.

In some embodiments of any of the kits described herein, the kit further includes a swab.

In some embodiments of any of the kits described herein, the kit further includes instructions to use the kit.

In some embodiments of any of the kits described herein, the kit further includes one or more of dNTPs or a mixture of dNTPs and ddNTPs.

In some embodiments of any of the kits described herein, the kit optionally includes reagent for extracting/isolating a nucleic acid from a biological sample.

In some embodiments, the template oligonucleotide includes one or more modified nucleotides, spacers, or blocking groups.

In some embodiments, at least one modified nucleotide includes a 2'modification.

In some embodiments, at least one modified nucleotide includes a 2'—O-methyl.

In some embodiments of any of the kits described herein, the kit further includes a polymerase.

The invention provides a highly sensitive and rapid qualitative assay for the detection and diagnosis of a RSV infection in a subject.

The term "template" or "primer" refers to an oligonucleotide that is capable of acting as a point of initiation for the 5' to 3' synthesis of a primer extension product that is complementary to a nucleic acid strand. The primer extension product is synthesized in the presence of appropriate nucleotides and an agent for polymerization, such as a DNA polymerase, in an appropriate buffer and at a suitable temperature.

As used herein, the term "probe" refers to an oligonucleotide that forms a hybrid structure with the product generated by amplification of the target nucleic acid sequence in a sample undergoing analysis, due to complementarity of at least one sequence in the probe with the target sequence. The nucleotides of any particular probe may be deoxyribonucleotides, ribonucleotides, and/or synthetic nucleotide analogs.

Within the context of the present invention, the target nucleic acid sequence is a nucleic acid sequence of RSV. For example, within the context of the present invention, the target nucleic acid sequence can be the nucleic acid sequence of the RSV nonstructural gene NS2 or the nucleic acid sequence of RSV the nucleocapsid gene N.

The term "one or more" or "at least one" as used in the present invention stands for 1, 2, 3, 4, 5, 6, 7, 8, 9, 10 compound(s) or even more.

The terms "first", "second", "third", and "fourth", etc. are used in this disclosure in their relative sense only. It will be understood that, unless otherwise noted, those terms are used merely as a matter of convenience in the description of one or more of the embodiments. The terms "first", "second", "third", and "fourth", etc. are only used to distinguish one element from another element, and the scope of the rights of the disclosed technology should not be limited by these terms. For example, a first element may be designated as a second element, and similarly the second element may be designated as the first element.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a reference level.

The terms "decrease", "decreased", "reduced", "reduction" or 'down-regulated" are all used herein generally to mean a decrease by a statistically significant amount. However, for avoidance of doubt, "reduced", "reduction", "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a reference level.

The section headings used herein are for organizational purposes only and are not to be construed as limiting the described subject matter in any way. When definitions of terms in incorporated references appear to differ from the definitions provided in the present teachings, the definition provided in the present teachings shall control. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and are not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
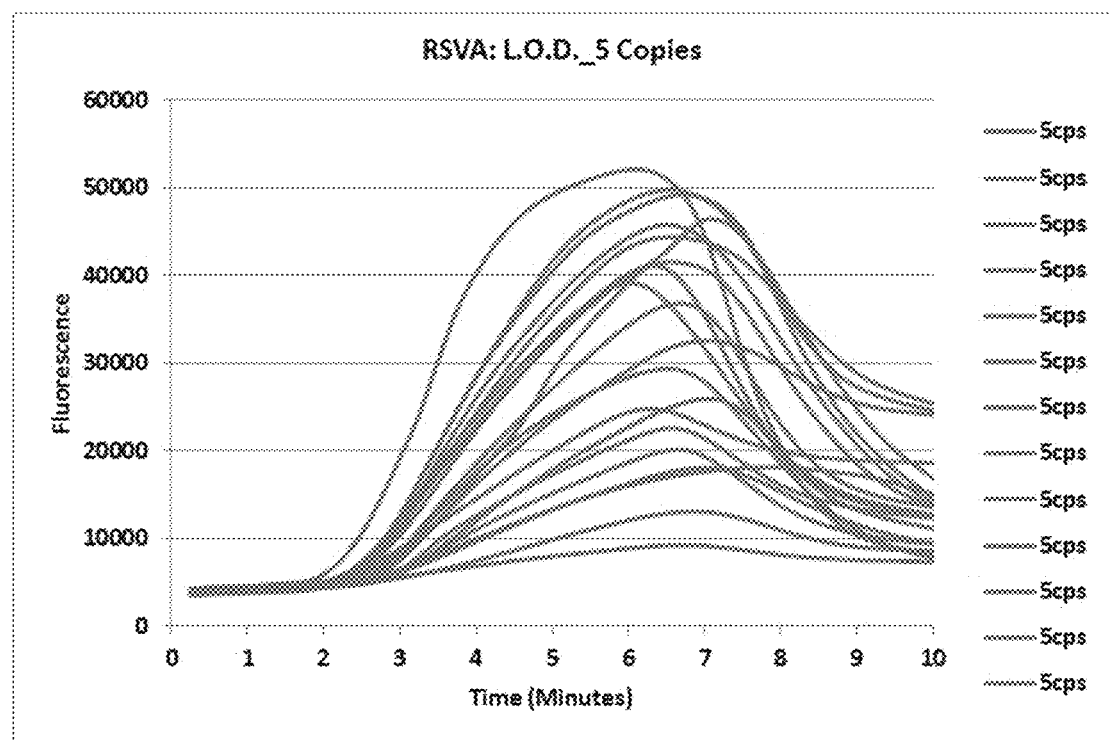
FIG. 1 is a graph showing the results of a limit of detection (LOD) study using an exemplary assay to detect RSV nonstructural gene NS2 ("RSV A assay") as described herein.

Provided herein are ultra-rapid, sensitive, specific, and robust approaches for use at point-of-care (POC). The isothermal nature of Nicking Enzyme Amplification Reaction, or NEAR, using either DNA or RNA targets, short products, and geometric amplification mechanism provide an ultra-rapid amplification method. The ability to provide robust performance in the presence of clinical matrix sets NEAR apart from most other molecular tests as there is no need for a lengthy or cumbersome sample preparation/ nucleic acid purification. These key attributes make NEAR an ideal technology for POC integration, where a rapid and reliable result is essential. Based on these principles, a NEAR test has been developed to detect the presence or absence of RSV in a sample. In an exemplary embodiment, the test consists of two assays, to detect nonstructural gene NS2 and/or nucleocapsid gene N, using clinical patient samples, e.g., nasal swab samples.

This disclosure is based in part on the discovery that it is possible to detect the presence or absence of RSV in a biological sample using isothermal amplification. To that end, the present application discloses a composition for detecting the presence or absence of RSV in a biological sample by amplifying and detecting a target nucleotide sequence using NEAR. In some embodiments, the target nucleotide sequence can be detected using real-time or end-point detection approaches, for example utilizing fluorescence labeled probes.

The use of the term "target sequence" may refer to either the sense or antisense strand of the sequence, and also refers to the sequences as they exist on target nucleic acids, amplified copies, or amplification products, of the original target sequence. The amplification product may be a larger molecule that comprises the target sequence, as well as at least one other sequence, or other nucleotides.

Methods of this invention can be used to identify nucleic acid from specimens for diagnosis of RSV infection. The specific primers and probes of the invention that are used in these methods allow for the amplification of and monitoring the development of specific amplification products. The increased sensitivity of NEAR for detection of RSV (e.g., nonstructural gene NS2, nucleocapsid gene N) make feasible the implementation of this technology for routine diagnosis of RSV infections in the clinical laboratory and at point-of-care.

Certain isothermal amplification methods are able to amplify target nucleic acid from trace levels to very high and detectable levels within a matter of minutes. Such isothermal methods, e.g., NEAR and RPA can allow users to detect a particular sequence in trace amounts, facilitating point-of-care testing and increasing the accessibility and speed of diagnostics.

The time that the amplification reaction is run may vary from, for example, within about 1 minute, or within about 2, 3, 4, 5, 6, 7, 8, 9, 10, 11, 12, 13, 14, 15, 16, 17, 18, 19 or 20 minutes. Longer reaction times may produce acceptable results where speed is not an issue. In sonic embodiments, the reaction is between 1-20 minutes, 1-15 minutes or 1-10, 1-8, 1-5, 1-2.5, 2.5-5, 2.5-8, 2.5-10, or 2.5-20 minutes. The amplification processes described herein are efficient, and in some embodiments, there is about $1 \times 10^6$-fold or more amplification, about $1 \times 10^7$-fold or more amplification, about $1 \times 10^8$-fold or more amplification, about $1 \times 10^9$-fold or more amplification, or about $1 \times 10^{10}$-fold or more amplification in the time frame of the reaction, for example, in 5, 10 or twelve minutes. The reaction is highly sensitive, and is able to detect, for example, as low as about 1, 2, 3, 4, 5, 6, 7, 8, 9, 10, 20, 30, 40, 50, 60, 70, 80, 90, or 100 copies, or more, in a sample, as many as 200, 500, 1,000, 5,000, or 10,000, or more copies in a sample, or, for example, may detect a target that is present at a concentration of, for example, about 3.32E-13 micromolar to about 3.32E-8 micromolar, about 1.66E-12 micromolar to about 3.32E-8 micromolar, about 3.32E 13 micromolar to about 3.32E-7 micromolar, or about 3.32E-13 micromolar to about 3.32E-6 micromolar.

NEAR methods are disclosed, e.g., in U.S. Pat. Nos. 9,617,586 and 9,689,031 each of which are incorporated herein by reference.

Nucleic acids (e.g., polynucleotides) suitable for amplification in connection with the present methods include double-stranded and single-stranded nucleic acid molecules, such as DNA and RNA molecules. The polynucleotides may be of genomic, chromosomal, plasmid, mitochondrial, cellular, and viral nucleic acid origin. For double stranded polynucleotides, the amplification may be of either one or both strands.

Another such isothermal amplification method suitable for the methods disclose herein is RPA. RPA can allow users to detect a particular sequence in trace amounts, facilitating point-of-care testing and increasing the accessibility and speed of diagnostics. As described here, RPA employs enzymes, known as recombinases, that are capable of pairing oligonucleotide primers with homologous sequences in template double-stranded nucleic acid. In this way, DNA synthesis is directed to defined points in a template double-stranded nucleic acid. Using two or more sequence-specific (e.g., gene-specific) primers, an exponential amplification reaction is initiated if the template nucleic acid is present. The reaction progresses rapidly and results in specific amplification of a sequence present within the template double-stranded nucleic acid from just a few copies of the template nucleic acid to detectable levels of the amplified products within minutes. RPA methods are disclosed, e.g., in U.S. Pat. Nos. 7,270,981; 7,399,590; 7,666,598; 7,435,561; 8,071, 308; and WO 2010/141940, all of which are incorporated herein by reference.

The terms "templates" and "primers" are used interchangeably and refer generally to an oligonucleotide sequence that serves as a starting point for nucleotide amplification of a target sequence using a polymerase. Templates are defined as oligonucleotides that bind to a recognition region of a target sequence and also contain a nicking enzyme binding region upstream of the recognition region and a stabilizing region upstream to the nicking enzyme binding region. The compositions disclosed herein can contain a set of templates that amplify the target nucleic acid sequence. The templates can comprise sequences that are complementary to the target nucleic acid sequence or that differ from the target nucleic acid sequence at one or more positions. Design of templates suitable for NEAR amplification methods disclosed herein are provided in, for example, U.S. Pat. Nos. 9,617,586 and 9,689,031, each of which are incorporated herein by reference.

The templates of the present methods may include, for example, spacers, blocking groups, and modified nucleotides. Modified nucleotides are nucleotides or nucleotide triphosphates that differ in composition and/or structure from natural nucleotides and nucleotide triphosphates. Modifications include those naturally occurring or that result from modification by enzymes that modify nucleotides, such as methyltransferases. Modified nucleotides also include synthetic or non-naturally occurring nucleotides. For example, modified nucleotides include those with 2' modifications, such as 2'—O-methyl and 2'-fluoro. Other 2'-modified nucleotides are known in the art and are described in, for example U.S. Pat. No. 9,096,897, which is incorporated herein by reference in its entirety. Modified nucleotides or nucleotide triphosphates used herein may, for example, be modified in such a way that, when the modifications are present on one strand of a double-stranded nucleic acid where there is a restriction endonuclease recognition site, the modified nucleotide or nucleotide triphosphates protect the modified strand against cleavage by restriction enzymes. Thus, the presence of the modified nucleotides or nucleotide triphosphates encourages the nicking rather than the cleavage of the double-stranded nucleic acid. Blocking groups are chemical moieties that can be added to the template to inhibit target sequence-independent nucleic acid polymerization by the polymerase. Blocking groups are usually located at the 3' end of the template. Examples of blocking groups include, for example, alkyl groups, non-nucleotide linkers, phosphorothioate, alkane-diol residues, peptide nucleic acid, and nucleotide derivatives lacking a 3'—OH, including, for example, cordycepin. Examples of spacers, include, for example, C3 spacers. Spacers may be used, for example, within the template, and also, for example, at the 5' end to attach other groups, such as, for example, labels.

In another aspect of the invention, there is provided a method for detection of RSV in a sample comprising the steps of obtaining a sample from a subject; extracting nucleic acids from the sample; and amplifying the nucleic acid; wherein the nucleic acid is amplified and detected with templates and probes as described herein.

The present invention further comprises detecting the amplification product, for example, by a method selected from the group consisting of gel electrophoresis, mass spectrometry, SYBR I fluorescence, SYBR II fluorescence, SYBR Gold, Pico Green, TOTO-3, intercalating dye detection, FRET, molecular beacon detection, surface capture, capillary electrophoresis, incorporation of labeled nucleotides to allow detection by capture, fluorescence polarization, and lateral flow capture. Amplification products can be detected, for example, by chemical moieties that intercalate into double-stranded DNA. For example, SYBR Green® binds double-stranded DNA and upon excitation emit light; thus as product accumulates, fluorescence increases. The amplification products may be, for example, detected using a solid surface method, for example, where at least one capture probe is immobilized on the solid surface that binds to the amplified sequence. In some embodiments of all aspects, detecting the amplified product is performed using "real-time fluorescence."

The term "real-time fluorescence," refers to the detection of nucleic acid amplification products via a fluorescent signal generated by the coupling of a fluorogenic dye molecule and a quencher moiety to the same or different oligonucleotide substrates. Examples of commonly used probes are TAQMAN® probes, Molecular Beacon probes, and SCORPION® probes. Briefly, TAQMAN® probes, Molecular Beacons, and SCORPION® probes each have a fluorescent reporter dye (also called a "fluor") and a quencher moiety attached in close proximity to one another. In the unhybridized state, the proximity of the fluor and the quencher molecules prevents the detection of fluorescent signal from the probe; in the case of TAQMAN® probes, during amplification, when the polymerase replicates a template on which a probe is bound, the 5'-nuclease activity of the polymerase cleaves the probe thus, increasing fluorescence with each replication cycle as the fluor and quencher are separated from one another. Molecular beacons probes emit fluorescence following annealing of a homologous product, as this event induces a conformational change in the structure of the beacon, thereby separating the fluor and quencher. Briefly, TAQMAN® probes and SCORPION® probes, similar to Molecular beacons, will release fluorescence signal when a specific product anneals to the probe and is extended, which leads to separation of the fluor and quencher.

The production or presence of target nucleic acids and nucleic acid sequences may also be detected and monitored by lateral flow devices. Lateral flow devices are well known. These devices generally include a solid phase fluid permeable flow path through which fluid flows through by capillary force. Examples include, but are not limited to, dipstick assays and thin layer chromatographic plates with various appropriate coatings. Immobilized on the flow path are various binding reagents for the sample, binding partners or conjugates involving binding partners for the sample and signal producing systems. Detection of samples can be achieved in several manners; enzymatic detection, nanoparticle detection, colorimetric detection, and fluorescence detection, for example. Enzymatic detection may involve enzyme-labeled probes that are hybridized to complementary or substantially complementary nucleic acid targets on the surface of the lateral flow device. The resulting complex can be treated with appropriate markers to develop a readable signal. Nanoparticle detection involves bead technology that may use colloidal gold, latex and paramagnetic nanoparticles. In one example, beads may be conjugated to an anti-biotin antibody. Target sequences may be directly biotinylated, or target sequences may be hybridized to sequence specific biotinylated probes. Gold and latex give rise to colorimetric signals visible to the naked eye and paramagnetic particles give rise to a non-visual signal when excited in a magnetic field and can be interpreted by a specialized reader.

Nucleic acids can also be captured on lateral flow devices. Means of capture may include antibody dependent and antibody independent methods. Antibody-dependent capture generally comprises an antibody capture line and a labeled probe that is complementary or substantially complementary sequence to the target. Antibody-independent capture generally uses non-covalent interactions between two binding partners, for example, the high affinity and irreversible linkage between a biotinylated probe and a Streptavidin line. Capture probes may be immobilized directly on lateral flow membranes. Both antibody dependent and antibody independent methods may be used in multiplexing.

The production or presence of target nucleic acids and nucleic acid sequences may also be detected and monitored by multiplex DNA sequencing. Multiplex DNA sequencing is a means of identifying target DNA sequences from a pool of DNA. The technique allows for the simultaneous processing of many sequencing templates. Pooled multiple templates can be resolved into individual sequences at the completion of process.

The terms "complementary" and "substantially complementary" refer to base pairing between nucleotides or nucleic acids, such as, for instance, between the two strands of a double-stranded DNA molecule or between an oligonucleotide primer and a primer binding site on a single-stranded nucleic acid to be sequenced or amplified. Complementary nucleotides are, generally, A and T (or A and U), and G and C. Within the context of the present invention, it is to be understood that the specific sequence lengths listed are illustrative and not limiting and that sequences covering the same map positions, but having slightly fewer or greater numbers of bases are deemed to be equivalents of the sequences and fall within the scope of the invention, provided they will hybridize to the same positions on the target as the listed sequences. Because it is understood that nucleic acids do not require complete complementarity in order to hybridize, the probe and primer sequences disclosed herein may be modified to some extent without loss of utility as specific primers and probes. Generally, sequences having homology of 80%, 90%, 95%, 97%, 98%, 99% fall within the scope of the present invention. As is known in the art, hybridization of complementary and partially complementary nucleic acid sequences may be obtained by adjustment of the hybridization conditions to increase or decrease stringency, i.e., by adjustment of hybridization temperature or salt content of the buffer.

In some embodiments of all aspects, the template and probes can be labeled with (e.g., conjugated to) a detectable label. The term "detectable label" and "label" as used herein refers to any chemical moiety that can be used to provide a detectable (preferably quantifiable) signal, and that can be attached to a nucleic acid or protein via a covalent bond or noncovalent interaction (e.g., through ionic or hydrogen bonding, or via immobilization, adsorption, or the like). Labels generally provide signals detectable by fluorescence, chemiluminescence, radioactivity, colorimetry, mass spectrometry, X-ray diffraction or absorption, magnetism, enzymatic activity, or the like. Examples of labels include haptens, enzymes, enzyme substrates, coenzymes, enzyme inhibitors, fluorophores, quenchers, chromophores, magnetic particles or beads, redox sensitive moieties (e.g., electrochemically active moieties), luminescent markers, radioisotopes (including radionucleotides), and members of binding pairs. More specific examples include fluorescein, phycobiliprotein, tetraethyl rhodamine, and beta-galactosidase. Binding pairs may include biotin/Streptavidin, biotin/avidin, biotin/neutravidin, biotin/captavidin, epitope/antibody, protein A/immunoglobulin, protein G/immunoglobulin, protein L/immunoglobulin, GST/glutathione, His-tag/Metal ion (e.g., nickel, cobalt or copper), antigen/antibody, FLAG/M1 antibody, maltose binding protein/maltose, calmodulin binding protein/calmodulin, enzyme-enzyme substrate, receptor-ligand binding pairs, and analogs and mutants of the binding pairs.

As used herein, the terms "fluorescence label" and "fluorophore" are used interchangeably and refer to any substance that emits electromagnetic energy at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals.

Representative fluorophores for use in the methods provided herein include, for example, FAM, (tetramethylrhodamine) Texas Red™, green fluorescent protein, blue fluorescent protein, red fluorescent protein, fluorescein, fluorescein 5-isothiocyanate (FITC), cyanine dyes (Cy3, Cy3.5, Cy5, Cy5.5, Cy7), Bodipy dyes (Invitrogen) and/or Alexa Fluor dyes (Invitrogen), dansyl, Dansyl Chloride (DNS-Cl), 5-(iodoacetamida)fluorescein (5-IAF, 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, rhodamine dyes (5-carboxyrhodamine 6G hydrochloride, Lissamine rhodamine B sulfonyl chloride, rhodamine-B-isothiocyanate (RITC (rhodamine-B-isothiocyanate), rhodamine 800); tetramethylrhodamine 5-(and 6-)isothiocyanate (TRITC)), Texas Red™, sulfonyl chloride, naphthalamine sulfonic acids including but not limited to 1-anilinonaphthalene-8-sulfonic acid (ANS) and 6-(p-toluidinyl)naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, Naphtyl Styryl, 3,3'dipropylthiadicarbocyanine (diS-C3-(5)), 4-(p-dipentyl aminostyryl)-1-methylpyridinium (di-5-ASP), Cy-3 lodo Acetamide, Cy-5-N-Hydroxysuccinimide, Cy-7-Isothiocyanate, IR-125, Thiazole Orange, Azure B, Nile Blue, A1 Phthalocyanine, Oxaxine 1, 4', 6-diamidino-2-phenylindole. (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofiuors, Coronene, and metal-ligand complexes.

It should be noted that a fluorescence quencher is also considered a detectable label. For example, the fluorescence quencher may be contacted to a fluorescent dye and the amount of quenching may be detected.

Haptens for use in the methods provided herein include, for example, digoxigenin, glutathione and biotin.

Enzymes for use in the methods provided herein include, for example, alkaline phosphatase (AP), beta-galactosidase, horse radish peroxidase (HRP), soy bean peroxidase (SBP), urease, beta-lactamase and glucose oxidase.

The compositions for detecting the presence or absence of RSV in a biological sample described herein, e.g., reagent mixtures, can include a DNA polymerase. The DNA polymerase disclosed herein may be a eukaryotic or prokaryotic polymerase. The polymerase may be selected from, for example, Geobacillus bogazici DNA polymerase, Bst DNA polymerase, Bst DNA polymerase (Large fragment), 9° Nm DNA polymerase, Phi29 DNA polymerase, DNA polymerase I (E. coli), DNA polymerase I, Large, (Klenow) fragment, Klenow fragment (3'-5' exo-), T4 DNA polymerase, T7 DNA polymerase, Deep VentR™ (exo-) DNA Polymerase, Deep VentR™ DNA Polymerase, DyNAzyme™ EXT DNA, DyNAzyme™ II Hot Start DNA Polymerase, Phusion™ High-Fidelity DNA Polymerase, Therminator™ DNA Polymerase, Therminator™ II DNA Polymerase, VentR® DNA Polymerase, VentR® (exo-) DNA Polymerase, RepliPHI™ Phi29 DNA Polymerase, rBst DNA Polymerase, rBst DNA Polymerase, Large Fragment (IsoTherm™ DNA Polymerase), MasterAmp™ AmpliTherm™ DNA Polymerase, Taq DNA polymerase, Tth DNA polymerase, Tfl DNA polymerase, Tgo DNA polymerase, SP6 DNA polymerase, Tbr DNA polymerase, DNA polymerase Beta, ThermoPhi DNA polymerase and Pyrophage 3173 (Lucigen), or combinations thereof.

The compositions for detecting the presence or absence of RSV in a biological sample described herein, such as reagent mixtures and buffered solutions, can include an antimicrobial agent or preservative. An antimicrobial agent can inhibit the growth of microorganisms and increase the shelf life of a reagent mixture or buffer solution. The antimicrobial agent can include benzalkonium chloride, 5-chloro-2-methyl-4-isothiazolin-3-one, 2-methyl-4-isothiazolin-3-one, ProClin® (e.g., ProClin 300®, ProClin® 950, etc.), azides, merthiolates, and/or antibiotics. In some embodiments, the antimicrobial agent includes 5-chloro-2-methyl-4-isothiazolin-3-one and 2-methyl-4-isothiazolin-3-one.

By "constant temperature," "isothermal conditions," "essentially isothermal," or "isothermally" is meant a set of reaction conditions where the temperature of the reaction is kept essentially or substantially constant during the course of the amplification reaction. An advantage of the amplification method of the present methods is that the temperature does not need to be cycled between an upper temperature and a lower temperature. The nicking and the extension reaction will work at the same temperature or within the same narrow temperature range. However, it is not necessary that the temperature be maintained at precisely one temperature. If the equipment used to maintain an elevated temperature allows the temperature of the reaction mixture to vary by a few degrees, or few tenths of a degree, such as, for example, less than 1 degree, 0.8 degrees, 0.6 degrees, 0.4 degrees, or 0.2 degrees, this is not detrimental to the amplification reaction, and may still be considered to be an isothermal reaction.

The present invention may be used for multiplex amplification. Thus, for example, in certain embodiments of the present invention at least two target sequences are capable of being amplified. The term "multiplex amplification" refers to the amplification of more than one nucleic acid of interest. By "capable of being amplified" is meant the amplification reaction comprises the appropriate templates and enzymes to amplify at least two target sequences. Thus, for example, the amplification reaction may be prepared to detect at least two target sequences, but only one of the target sequences may actually be present in the sample being tested, such that both sequences are capable of being amplified, even though only one sequence may actually be amplified. Or, where two target sequences are present, the amplification reaction may result in the amplification of both of the target sequences. The multiplex amplification reaction may result in the amplification of one, some, or all, of the target sequences for which it comprises the appropriate templates and enzymes.

As used herein, the term "biological sample" or "sample" refers to a sample obtained or derived from a subject (i.e., a patient). By way of example, the biological sample may be a tissue fluid obtained from a subject, which may be selected from the group consisting of blood, plasma, serum, lymphatic fluid, synovial fluid, cerebrospinal fluid, amniotic fluid, amniotic cord blood, tears, saliva, mucus secretions, urine and nasopharyngeal washes. Representative biological samples from the respiratory tract include wound and throat swabs, throat washings, nasal swabs, and specimens from the lower respiratory tract.

As used herein, "obtain" or "obtaining" can be any means whereby one comes into possession of the sample by "direct" or "indirect" means. Directly obtaining a sample means performing a process (e.g., performing a physical method such as extraction) to obtain the sample. Indirectly obtaining a sample refers to receiving the sample from another party or source (e.g., a third party laboratory that directly acquired the sample). Directly obtaining a sample includes performing a process that includes a physical change in a physical substance, e.g., a starting material, such as a blood, e.g., blood that was previously isolated from a patient. Thus, obtain is used to mean collection and/or removal of the sample from the subject. Furthermore, "obtain" is also used to mean where one receives the sample from another who was in possession of the sample previously.

Target sequences present within target nucleic acids in a sample can be amplified with the methods of the invention without first purifying the target nucleic acids after the sample is obtained. The term "purify" can mean, for example, substantially separating target nucleic acids from inhibitors and background materials present in a sample. In accordance with the invention, obtained samples may be diluted, for example with a buffer suitable to lyse cells in the sample, without concentrating the target nucleic acid or substantially removing any inhibitors and background materials present in the sample.

The term "subject" refers to an animal or human, or to one or more cells derived from an animal or human. Preferably, the subject is a human. Subjects can also include non-human primates. Cells may be in any form, including but not limited to cells retained in tissue, cell clusters, immortalized, transfected or transformed cells, and cells derived from an animal that has been physically or phenotypically altered. A human subject can be known as a patient.

In yet other embodiments, a kit is provided for following the methods of the present invention for nucleic acid amplification, comprising a DNA polymerase; a first template for nucleic acid amplification, comprising a recognition region at the 3' end that is complementary or substantially complementary to the 3' end of a target sequence antisense strand; a nicking enzyme binding site and a nicking site upstream of the recognition region; and a stabilizing region upstream of the nicking enzyme binding site and the nicking site; a second template for nucleic acid amplification, comprising a recognition region at the 3' end that is complementary or substantially complementary to the 3' end of a target sequence sense strand; nicking enzyme binding site and a nicking site upstream of the recognition region; and a stabilizing region upstream of the nicking enzyme binding site and the nicking site; one or more nicking enzymes, wherein either one enzyme is capable of nicking at the nicking site of the first and said second templates, or a first enzyme is capable of nicking at the nicking site of the first template and a second enzyme is capable of nicking at the enzyme site of the second template.

The kits used for the present methods may also comprise one or more of the components in any number of separate containers, packets, tubes, vials, microtiter plates and the like, or the components may be combined in various combinations in such containers.

The components of the kit may, for example, be present in one or more containers, for example, all of the components may be in one container, or, for example, the enzymes may be in a separate container from the templates. The components may, for example, be lyophilized, freeze dried, or in a stable buffer. In one example, the polymerase and nicking enzymes are in lyophilized form in a single container, and the templates are either lyophilized, freeze dried, or in buffer, in a different container. Or, in another example, the polymerase, nicking enzymes, and the templates are, in lyophilized form, in a single container. Or, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits used for the present methods may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Kits may further comprise reagents used for detection methods, such as, for example, reagents used for FRET, lateral flow devices, dipsticks, fluorescent dye, colloidal gold particles, latex particles, a molecular beacon, or polystyrene beads.

An advantage of the present methods and the present kits is that they can be used in any device that provides a constant temperature, including thermocyclers, incubation ovens, water baths, and heat blocks.

Methods using capture probes for detection include, for example, the use of a nucleic acid molecule (the capture probe) comprising a sequence that is complementary to, or substantially complementary to, an amplification product strand such that the capture probe binds to amplified nucleic acid. The probe may be linked to a detectable label in certain embodiments, and amplification product may be detected based on the detectable label of the probe specifically hybridized to the amplification product. The reaction may, for example, further comprise an antibody directed against a molecule incorporated into or attached to the capture probe. Or, for example, the capture probe, or a molecule that binds to the capture probe, may incorporate, for example, an enzyme label, for example, peroxidase, alkaline phosphatase, or beta-galactosidase, a fluorescent label, such as, for example, fluorescein or rhodamine, or, for example, other molecules having chemiluminescent or bioluminescent activity. In some embodiments, the probe is linked to a solid support, and amplification product strands may be specifically immobilized to the capture probe linked to the solid support under conditions known and selected by the person of ordinary skill in the art. In the latter embodiments, a solid support-immobilized amplification product may be subjected to processing steps, such as washing, ion exchange, release from the solid support, or other processing steps. An amplification product may be detected when immobilized to a solid support in some embodiments. The embodiments of the present invention also comprise combinations of these detection and analysis methods.

In yet another embodiment, the methods further comprise modifying the subject's clinical record to identify the subject as being diagnosed as having a RSV infection. Preferably, the clinical record is stored in a computer readable medium.

EXAMPLES

The invention is further described in the following examples, which do not limit the scope of the invention described in the claims. Those of ordinary skill in the art understand that for an exemplary assay, numerous modifications may be made to the volumes and format of the reaction, the length of time that the assay is conducted, and the amounts of each reactant.

Example 1. NEAR of RSV Genomic DNA

Target Selection

NEAR assays targeting nonstructural gene NS2 and gene N were developed that are unique to RSV while showing strong conservation across multiple RSV strains. Initial bioinformatics analyses were performed using sequence data available from NCBI's Nucleotide Database (www.ncbi.nlm nih.gov/nuccore) and Genome Database (www.ncbi.nlm nih.gov/genome?db=genome). Multiple sequence alignments were performed to identify regions of conservation. All sequence segments demonstrating homology were subjected to BLAST analysis to determine whether these sequences were unique to RSV. Following BLAST analyses, all sequences identified as unique to RSV were used for template set generation (BLAST analysis performed using the nucleotide collection (nr/nt) database). Template sets were generated in part by using an in-house automated software tool. In silico filtering was then applied to finalize the selection of template sets to screen in the laboratory. In general, these filtering criteria involved analyzing the template sets for potential interactions that could reduce assay performance, including several parameters identified in-house that might specifically impact NEAR performance as well as parameters that are common to most nucleic acid amplification technologies. Using these filtering criteria, a set of "RSV A" and "RSV B" templates were selected for screening.

The screening process resulted in the development of the following assay for detecting RSV. The assay amplifies at least one RSV target nucleic acid, the nonstructural gene NS2 located at nucleotide position 780-817 of reference strain NC_001803.1; and/or the nucleocapsid gene N located at position 1220-1261 of reference strain N2 KF893260.1. The NS2 gene encodes for the nonstructural 2 protein (NS2), which is responsible for inhibiting host type I interferon activity (to help evade the immune system). The N gene encodes for the nucleocapsid protein, which aids in viral replication and transcription.

The "RSV A" assay targets nucleotide position 780-817 of the RSV reference strain NC_001803.1 (within the NS2 gene) and the "RSV B" assay targets nucleotide position 1220-1261 of the RSV reference strain N2 KF893260.1. The assay templates, probe (molecular beacon) and product sequences are provided in Tables 1 and 2 below.

TABLE 1

RSV A assay details

| ID | Sequence 5'-3' | SEQ ID NO: | Condition |
|---|---|---|---|
| RSV A template T1 | CGACTCACACGAGTCGAAAACT TGATGAAAGA | 1 | 400 nM |

TABLE 1-continued

RSV A assay details

| ID | Sequence 5'-3' | SEQ ID NO: | Condition |
|---|---|---|---|
| RSV A template T2.OM1 | AGACTCCACACGGAGTCTAG TTmGmACCAGGAATG | 2 | 100 nM |
| RSV molecular beacon MB_Rox3OMe | ACCAGGAATGmTAAAmTGT GGmCCTGGT | 3 | 200 nM |
| RSV A P1 | ACTTGATGAAAGACAGGCCAC ATTTACATTCCTGGTCA | 4 | |
| RSV A P2 | TGACCAGGAATGTAAATGTG GCCTGTCTTTCATCAAGT | 5 | | m = 2'-O-methyl modified nucleotide (m precedes modified nucleotide in IDT nomenclature)
bold = spacer sequence for target product

TABLE 2

RSV B assay details

| ID | Sequence 5'-3' | SEQ ID NO: | Condition |
|---|---|---|---|
| RSV B template T1 | GACTCGCACACGAGTCACGTAGT ACAGGAGATAA | 6 | 600 nM |
| RSV B Template T2 | GACTCCACACGGAGTCGCTTTTG CACATCATAA | 7 | 100 nM |
| RSV B molecular beacon MB_Rox 2OMe | TGACACATCATAAmTTGGGmAGT GTCA | 8 | 200 nM |
| RSV B internal control (IC) molecular beacon MB_Fam | CCGTCAACCACACACCTGACGG | 9 | 200 nM |
| RSV B IC | AU*U*U*GCACAUCAUAA*CCACA CACCUGACGUUAUCUCCUGUAC* U*AC*A | 10 | 40K copies |
| RSVB P1 | AGTACAGGAGATAATATTGACA CTCCCAATTATGATGTGCAA | 11 | |
| RSV B P2 | TTGCACATCATAATTGGGAGTG TCAATATTATCTCCTGTACT | 12 | |
| RSV B IC P1 | AGTACAGGAGATAA<u>CGTCAGGT GTGTGG</u>TTATGATGTGCAA | 13 | |
| RSV BIC P2 | TTGCACATCATAA<u>CCACACACCT GACG</u>TTATCTCCTGTACT | 14 | | m = 2'-O-methyl modified nucleotide (m precedes modified nucleotide in IDT nomenclature)
\* = phosphorothioate bond
bold = spacer sequence for target product
<u>underlined</u> = spacer sequence for internal control (IC) product
*italics* = spacer sequence of internal control (IC) target To confirm that the assay target sequences are conserved among all respective RSV A and B sequences found in the public domain as well as unique to RSV, multiple sequence alignments and BLAST analyses were performed. Multiple alignment analyses of these sequences revealed good homology across all sequences found in the public domain, for both the RSV A and RSV B assays. Upon BLAST analysis, it was confirmed that no other species contain significant homology to the RSV A & B target sequences. To note, the RSV A target did show significant homology to the RSV B genome, and the RSV B target sequence did show significant homology to the RSV A genome.

RSV Test Format

The RSV NEAR assays were developed to run on the Alere™ i platform. The Alere™ i platform consists of the Alere™ i instrument which provides heating, mixing and fluorescence detection with automated result output, and a set of disposables, consisting of the sample receiver (where the elution/lysis buffer is stored), a test base (containing two tubes of lyophilized NEAR reagents) and a transfer cassette (designed to transfer 100 µl aliquots of eluted sample from the sample receiver to each of the two tubes containing lyophilized NEAR reagents located in the test base).

The RSV assay is a two tube assay—a RSV A target specific assay in one tube, and a RSV B/internal control (IC) duplex assay in a second tube (tested side by side on the Alere™ i instrument in the test base).

The elution/lysis buffer (stored in the sample receiver) was designed to allow for the rapid release of RSV organisms from clinical sample nasal/nasopharyngeal swabs as well as to provide rapid and efficient lysis (strong acid), while also including the necessary salts for driving the NEAR assay (both $MgSO_4$ and $(NH_4)_2SO_4$).

During assay development, studies were undertaken to compare 2× vs. 3× vs. 4× lyophilization volume mixes. From these studies, it was determined that the 3× mix volume provided the best combination of performance and stability, and as a result, the 3× mix was selected to move forward into feasibility. Also during assay development, the length of time needed for pre-heating the elution/lysis buffer was analyzed. Pre-heat times of 1 minute, 2 minute and 3 minutes were compared, and from these data it was concluded that the best performing condition was a pre-heat step of 3 minutes.

Figure 2:
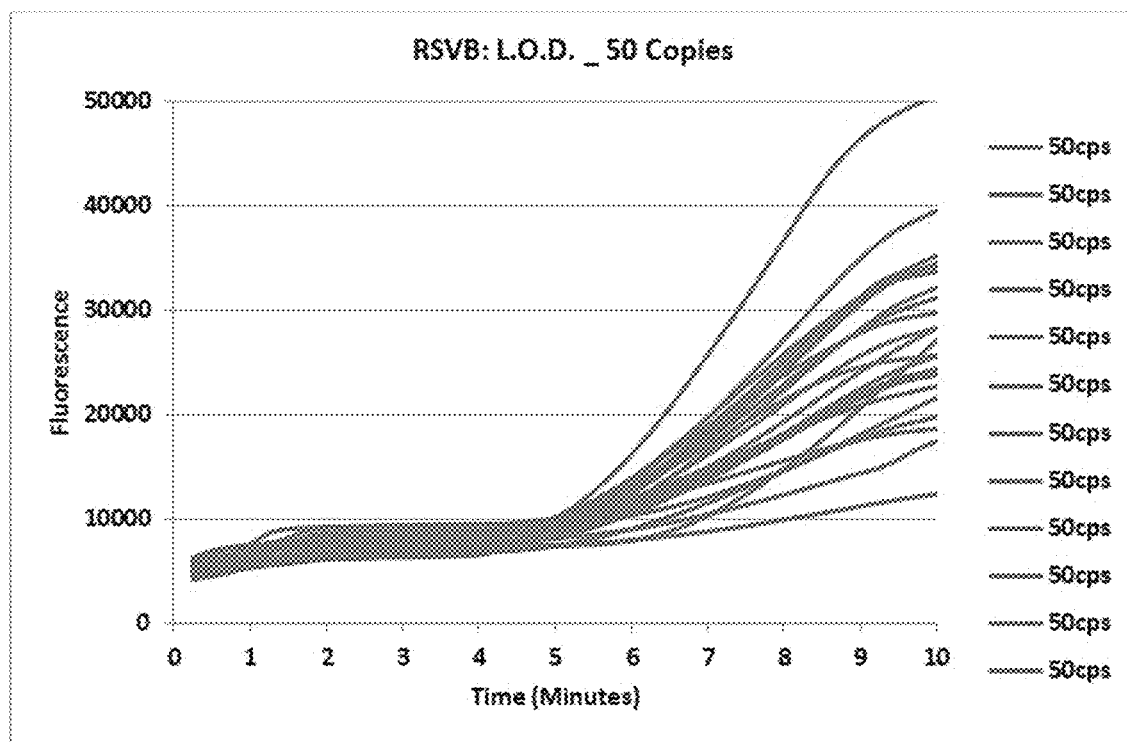
FIG. 2 is a graph showing the results of a LOD study performed using an exemplary assay to detect RSV nucleocapsid gene N ("RSV B assay") as described herein.

FIG. 1 and FIG. 2 show the results of a LOD study performed using the RSV A and RSV B assays using purified viral RNA, respectively. Purified RNA stock was diluted to appropriate concentrations so that 5 µl volumes added to 100 µl of rehydration buffer provided the appropriate copy number of target. Reactions were performed on the Stratagene Mx3005P thermal cycler using a standard 'hot start' approach. The LOD study was performed using a standard NEAR 'hot start' approach where the sample and lyophilized mix were both pre-heated at 56° C. for 3 minutes and then combined. From FIG. 1, it was concluded that the LOD is 5 copies of purified viral RNA of RSV A, when a standard 'hot start' approach is used. From FIG. 2, it was concluded that the LOD is 50 copies of purified viral RNA of RSV B, when a standard 'hot start' approach is used.

Internal Control

The presence of an internal control (IC) is a required component of a POC diagnostic device. For NEAR, the internal control provides verification that the assay reagents are functioning properly and have not been inactivated or inhibited during a test. This is particularly important when a clinical sample has been called 'negative'. To ensure that the 'negative' call is not due to assay failure, but rather due to the fact that the target organism is not present, an IC is essential. The RSV test is a two tube test, with RSV A detection occurring in one tube and RSV B detection in a second tube. Instead of incorporating controls into each tube, a single IC was incorporated into the tube containing the RSV B assay. The IC system consists of a set of templates, which are shared by the RSV B assay, a unique short RNA oligonucleotide target and an IC product-specific molecular beacon (Table 2). The RNA oligonucleotide contains 5' and 3' ends that are complementary to the target template set's recognition regions but with a spacer region that differs from the target's spacer region. Simply put, the same template set is used to amplify both target and IC.

Lyophilization

In order to provide a viable POC technology, the reagents used for RSV detection need to be stable for an extended period (e.g., six months to thirty-six months) of time at ambient temperature (up to 30° C.), or at minimum, when stored at 2-8° C. In order to provide this level of stability, the NEAR assay reagents need to be lyophilized and subsequently packaged to minimize reagent exposure to both moisture and oxygen.

To accomplish this, the NEAR assay reagents were combined in a mix containing the excipients dextrose and trehalose and subjected to freeze drying. Optimization of both the mix composition and freeze drying method were performed to yield a suitable lyophilized mix that retained activity while providing long term stability. The final lyophilization mix composition and freeze drying method selected to move forward with are shown below, in Tables 3 and 4, respectively. The RSV test format provides for two tubes, one tube providing the RSV A target assay and a second tube providing both the RSV B and IC assays. These reagents are freeze dried using the same lyophilization method and contain essentially the same set of reagents (excluding the fact that each tube contains a unique set of oligonucleotides for target and/or IC specific amplification and detection).

TABLE 3

RSV A and RSV B Lyophilization Mixes—Reagent Composition

| Reagent | [1×] RSV A | [1×] RSV B + IC |
|---|---|---|
| 500Kd Dextran | 1.67% | 1.67% |
| Trehalose | 33.3 mM | 33.3 mM |
| Water, nuclease free | — | — |
| Tris pH 9.0 | 40 mM | 40 mM |
| Tris pH 8.0 | 60 mM | 60 mM |
| $Na_2SO_4$ | 25 mM | 40 mM |
| Triton X-100 | 0.02% | 0.02% |
| EDTA | 0.5 mM | 0.5 mM |
| dNTPs | 0.3 mM | 0.3 mM |
| DTT | 2 mM | 2 mM |
| DNA poll (MG79) | 3.6 µg | 4.4 µg |
| N.BspD6 I | 0.2 µg | 0.2 µg |
| EIAV RT | 2.4 µg | 3.2 µg |
| 50X T/MB | 1X | 1X |
| IC RNA | — | 40 K copies |
| Polyacrylic Acid | — | 20 µg |

TABLE 4

RSV B Lyophilization Method-Thermal Treatment and Drying Protocol

| Method | Step | Temp (° C.) | Time (min) | Pressure (mT) | Note |
|---|---|---|---|---|---|
| Thermal Treatment | 1 | 5 | 5 | Atm | Pre-chill |
| | 2 | −50 | 120 | Atm | Ramp |
| | 3 | −50 | 30 | Atm | Hold |
| | 4 | −30 | 60 | Atm | Ramp |
| Primary Drying | 1 | −30 | 1100 | 50 | Hold |
| | 2 | −15 | 500 | 80 | Ramp |
| | 3 | 10 | 90 | 80 | Ramp |
| | 4 | 40 | 30 | 80 | Ramp |
| Secondary Drying | 1 | 40 | 120 | 80 | Hold |
| | 2 | 20 | 15 | 80 | Ramp |
| | 3 | 20 | 1255 | 80 | Hold |

Both mixes are lyophilized at 3× (33.3 µl), meaning that the mixes are dried down at a 3× concentration and subsequently re-suspended in a 100 µl volume to provide a final 1× concentration of each reagent. This approach effectively reduces the concentration of the two excipients added to each mix (dextran and trehalose) by three-fold, vs. if a 1× mix was used for freeze drying. The final step in the process of maximizing the stability of lyophilized NEAR material is packaging. Once the lyophilization process is completed, the dried reagents are exposed to an atmosphere of less than 10% relative humidity, whereupon they are pouched in a moisture-resistant and oxygen-resistant foil pouch containing a desiccant. The reagents can then be stored for an extended period of time without an obvious loss in performance.

RSV Elution/Lysis

To detect the presence of RSV, two steps precede target amplification and detection, elution of virus from the swab used to collect the clinical sample and lysis of the virus after elution or storage in universal transport media (UTM), to allow access to the target viral RNA genome. For a POC product, the elution and lysis must be efficient, rapid and simple. The inventors developed an acid-based elution and lysis buffer that effectively removes RSV virus from a swab and rapidly and efficiently lyses the viral shell to expose the viral genomic RNA for NEAR amplification. The buffer composition is shown in Table 5. These reagents provide sufficient elution and lysis for sensitive NEAR performance, as will be shown in subsequent sections of this document.

TABLE 5

Elution/Lysis Buffer Composition

| Reagent | [ ] |
| --- | --- |
| HCL | 20 mM |
| Triton X-100 | 0.10% |
| $(NH_4)_2 SO_4$ | 15 mM |
| $MgSO_4$ | 15 mM |
| Water, nuclease free | — |

The elution/lysis buffer is pre-heated for 3 minutes on the Alere™ i instrument, reaching a temperature of approximately 42° C.-45° C. At this time, either a 200 μl aliquot of UTM is added to the elution/lysis buffer and mixed, or a swab is briefly swirled (10 seconds) and expressed in the elution/lysis buffer. As will be described in later sections of this document, the elution/lysis buffer has been shown to effectively elute/lyse RSV from swabs and lyse RSV transferred from UTM, enabling sensitive NEAR amplification and detection following re-suspension of NEAR lyophilized material.

Example 2. Impact of Human Genomic DNA on RSV A/B NEAR Assay Performance

One potential inhibitor of the NEAR technology is human gDNA. When a nasal swab sample is collected from a patient symptomatic for RSV infection, it is possible that human gDNA is also collected on the swab (from immune cells such as white blood cells or from local epithelial cells). In order to assess the impact that human gDNA has on RSV A, RSV B and RSV B+IC assay performance, a study was undertaken where increasing amounts of purified human gDNA were added to each assay and both target and IC detection were monitored (FIGS. 3A-D; FIGS. 4A-D; and FIG. 5).

Figure 3A:
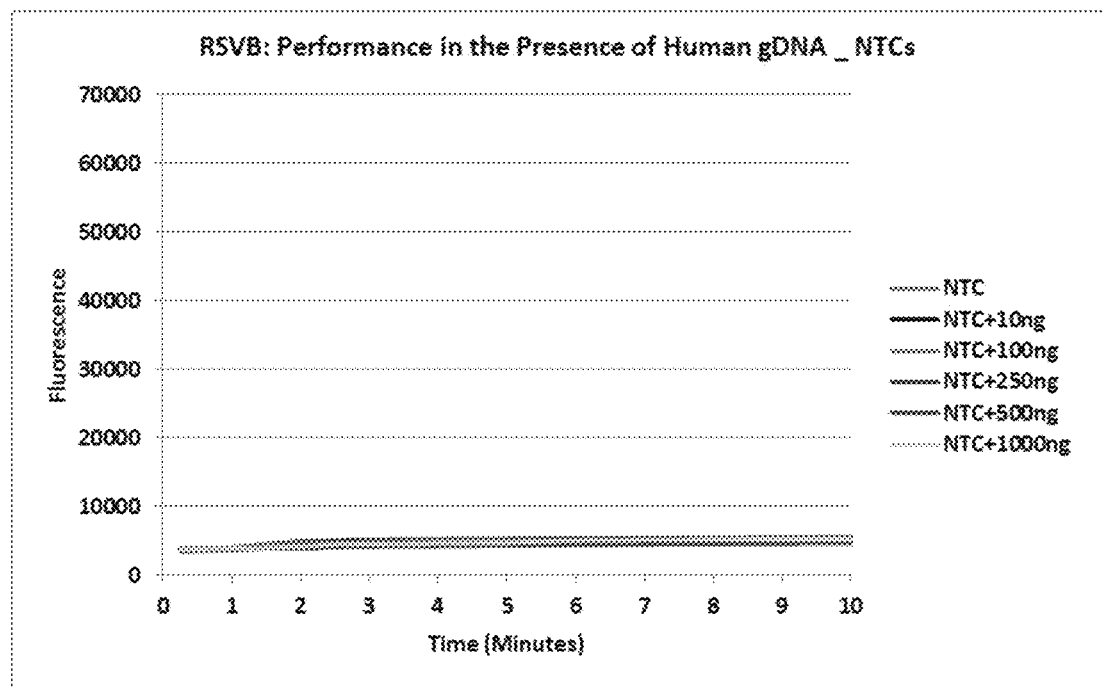
FIG. 3A-D are graphs showing the results of an exemplary RSV A assay performed in the presence of 0 copies (no target copies "NTC") (FIG. 3A), 50 copies (FIG. 3B), 250 copies (FIG. 3C), or 500 copies FIG. 3D) of the target nucleic acid and increasing amounts of background human genomic DNA (10 ng, 100 ng, and 1000 ng).
Figure 3B:
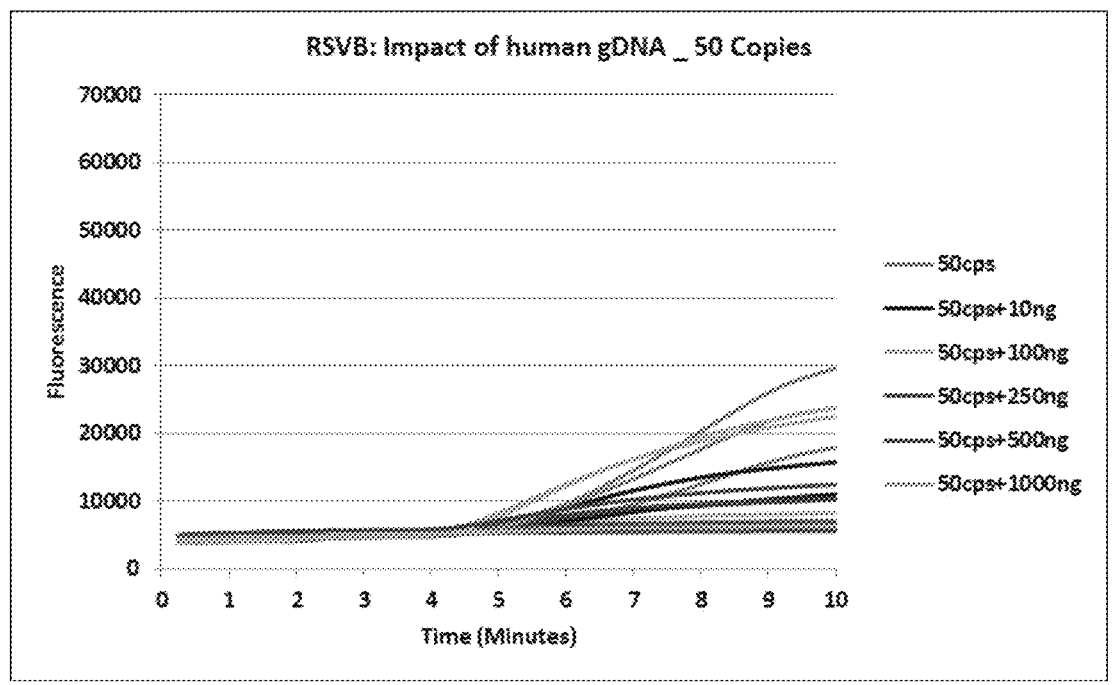
Figure 3C:
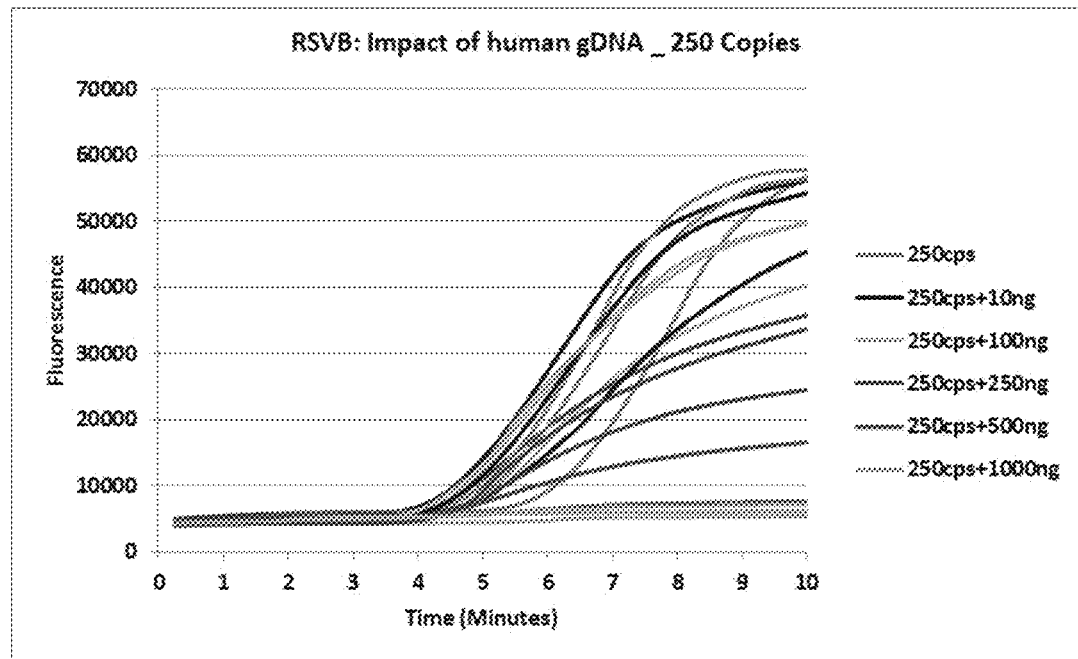
Figure 3D:
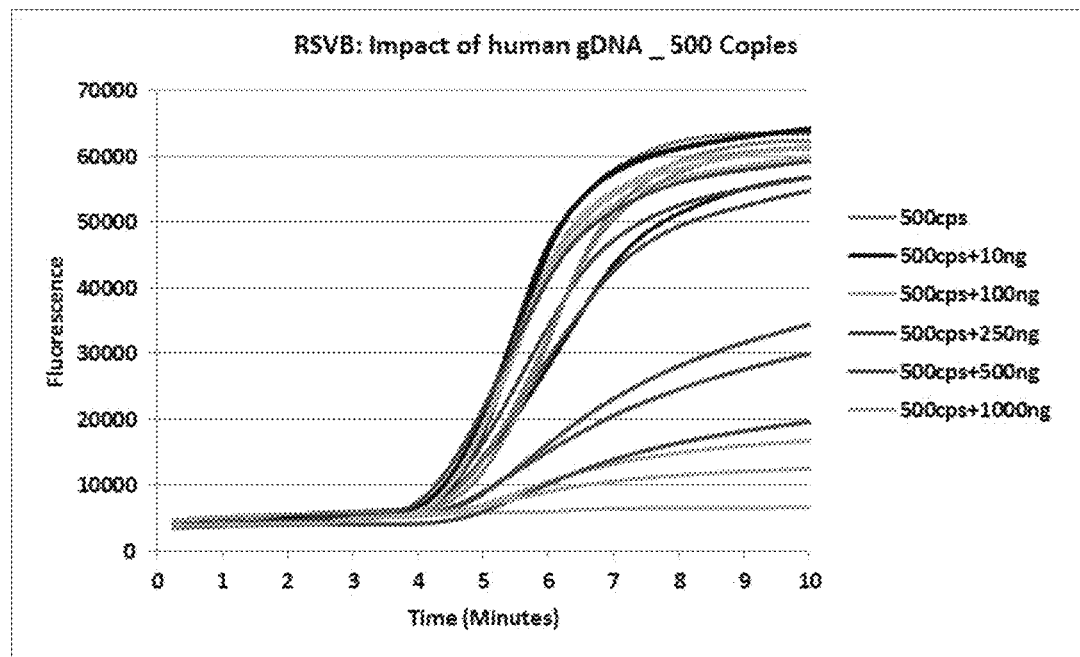

As shown in FIGS. 3A-D, the presence of human gDNA did not generate false positives as the fluorescence signal stayed at a baseline level regardless of the human gDNA input (from 0 to 1000 ng per reaction) when NTC reactions were tested. At the RSV A assay LOD (5 copies), the impact of human gDNA was strong. Although 5 copies of target were still detectable at 10 ng of human gDNA, all input levels of human gDNA above this amount led to virtually complete inhibition (FIG. 3B). As the copy number of target is increased, assay performance significantly improves in the presence of higher levels of human gDNA (FIGS. 3C-D), suggesting a competition between target amplification and non-specific consumption of critical reagents is occurring. As the target copy number is increased, the critical reagents are more likely being consumed for target-specific amplification and detection, and not being used for non-specific activities on human gDNA.

Figure 4A:
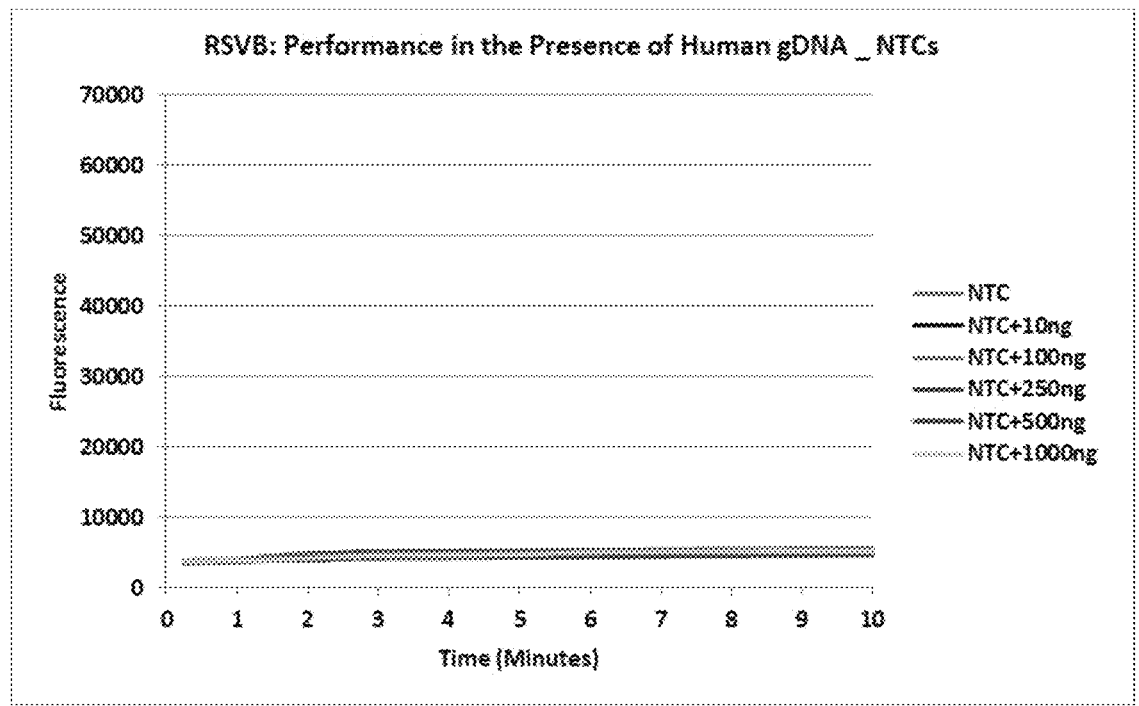
FIG. 4A-D are graphs showing the results of an exemplary RSV B assay performed in the presence of 0 copies ("NTC") (FIG. 4A), 50 copies (FIG. 4B), 250 copies (FIG. 4C) or 500 copies (FIG. 4D) of the target nucleic acid and increasing amounts of background human genomic DNA (10 ng, 100 ng, and 1000 ng).
Figure 4B:
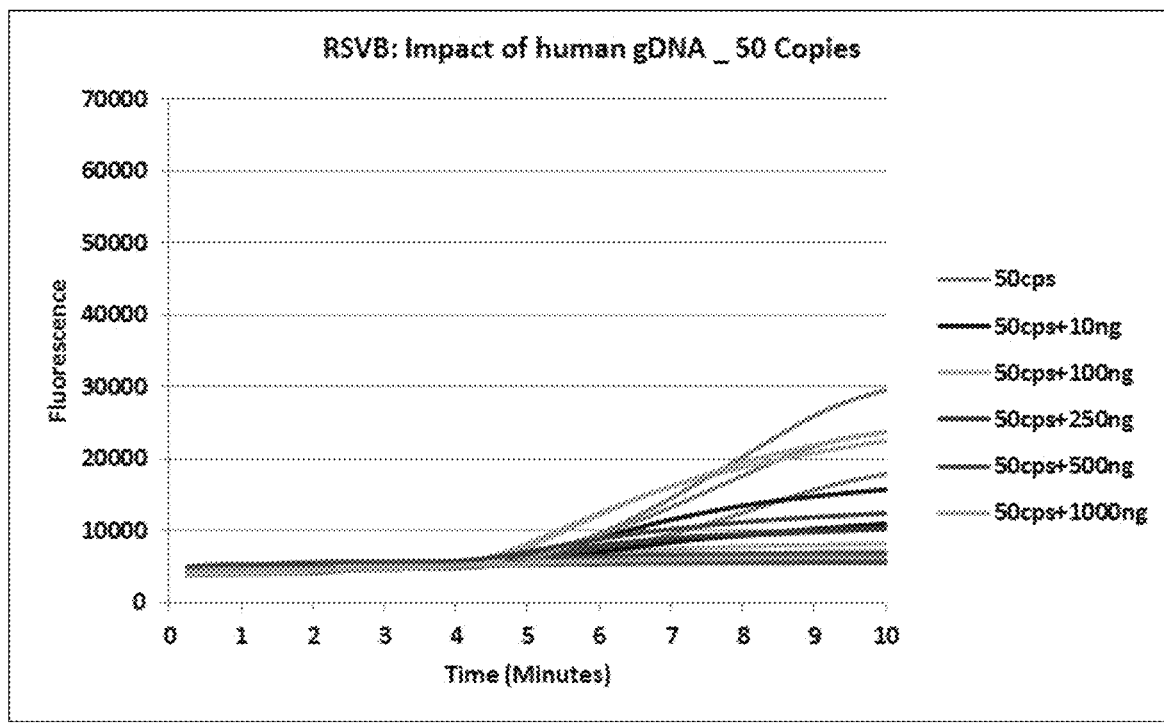
Figure 4C:
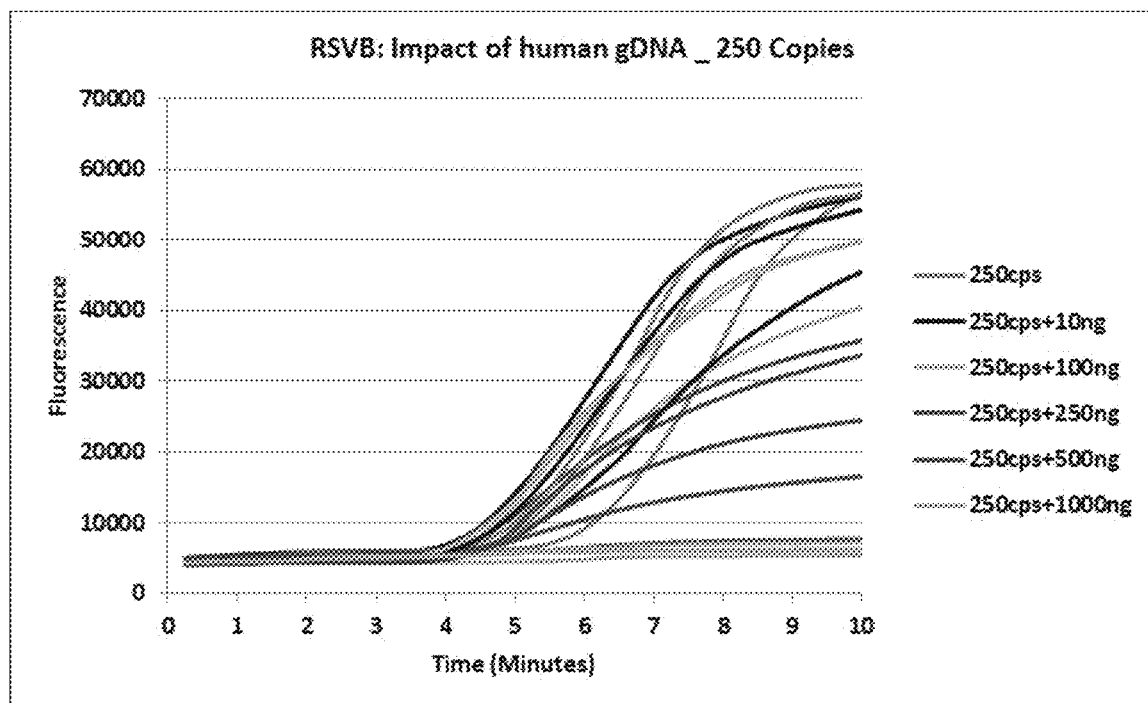
Figure 4D:
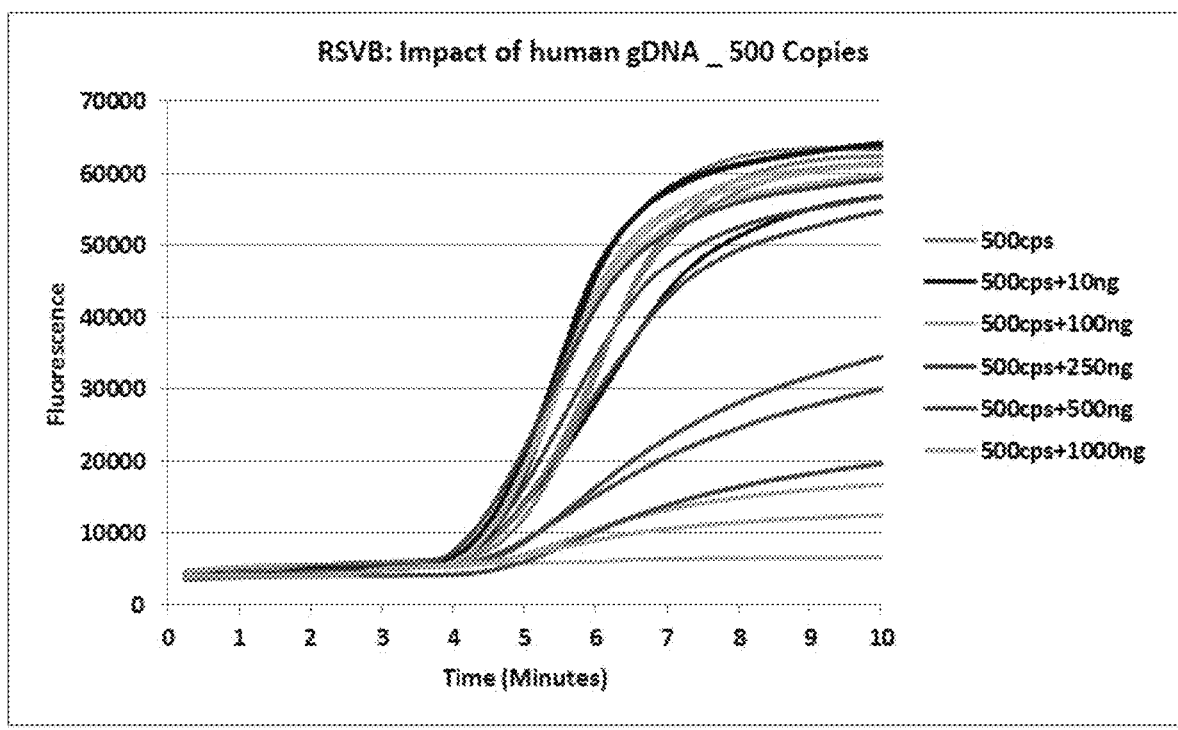

In FIGS. 4A-D, the presence of human gDNA did not generate false positives as the fluorescence signal stayed at a baseline level regardless of the human gDNA input (from 0 to 1000 ng per reaction) when NTC reactions were tested. At the RSV B assay LOD (50 copies), the impact of human gDNA was strong, with all input levels of human gDNA causing virtually complete inhibition (FIG. 4B). As the copy number of target is increased, assay performance significantly improves in the presence of higher levels of human gDNA (FIGS. 4C-D), suggesting a competition between target amplification and non-specific consumption of critical reagents is occurring (as described above).

Figure 5:
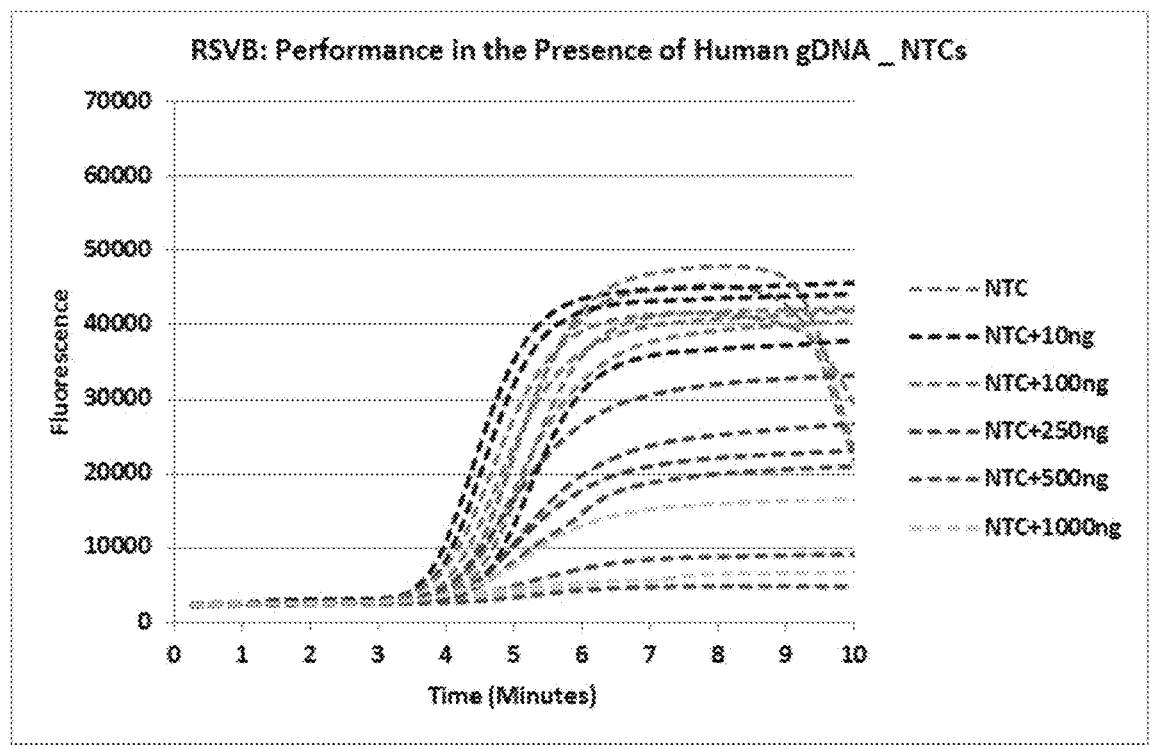
FIG. 5 is a graph showing the results of an exemplary RSV B assay performed with 0 copies of target nucleic acid in the presence of increasing amounts of background human gDNA (0, 10 ng, 100 ng, 1000 ng).

In FIG. 5, the RSV B+IC assay was performed in the presence of 0 copies of target (NTC reactions) and increasing amounts of human gDNA. The IC assay showed very good performance when stressed by the presence of 100 ng of human gDNA.

Example 3. Analytical Reactivity (Purified RNA) on Alere™ i-RSV A

Figure 6:
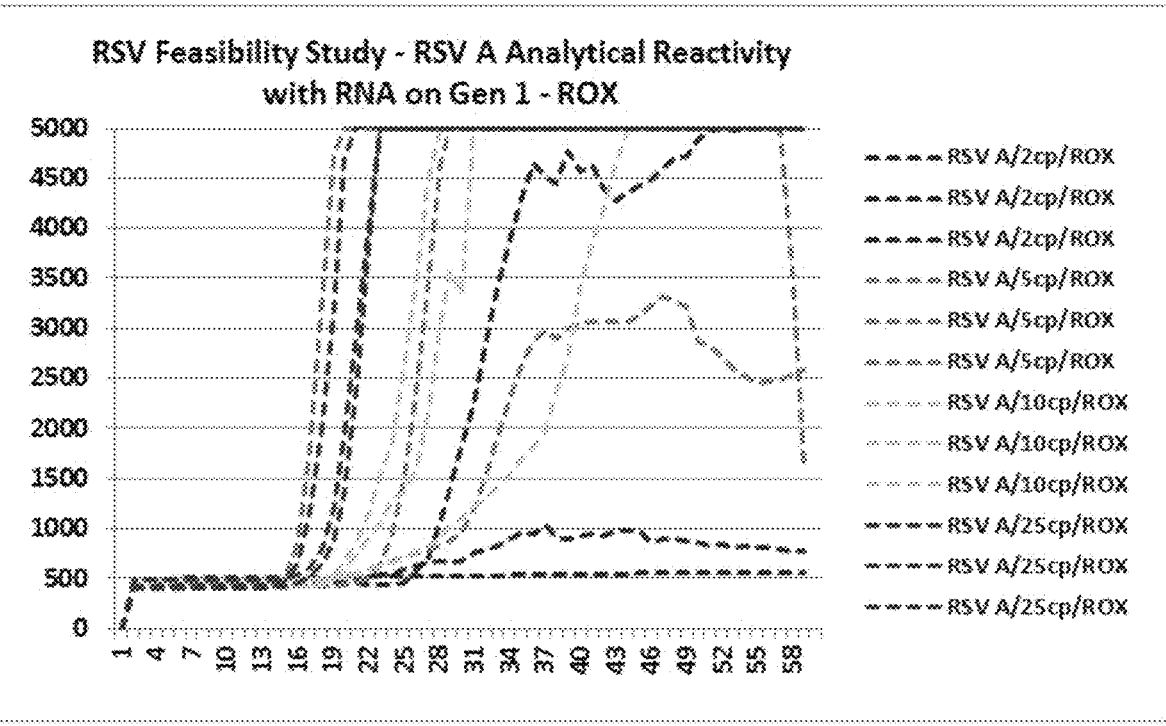
FIG. 6 and FIG. 7 are graphs showing the results of an exemplary RSV A assay to determine the assay's reactivity with purified RNA (FIG. 6) and purified virus (FIG. 7). X-axis—cycles (1 cycle=10 seconds); Y-axis—mV.
Figure 7:
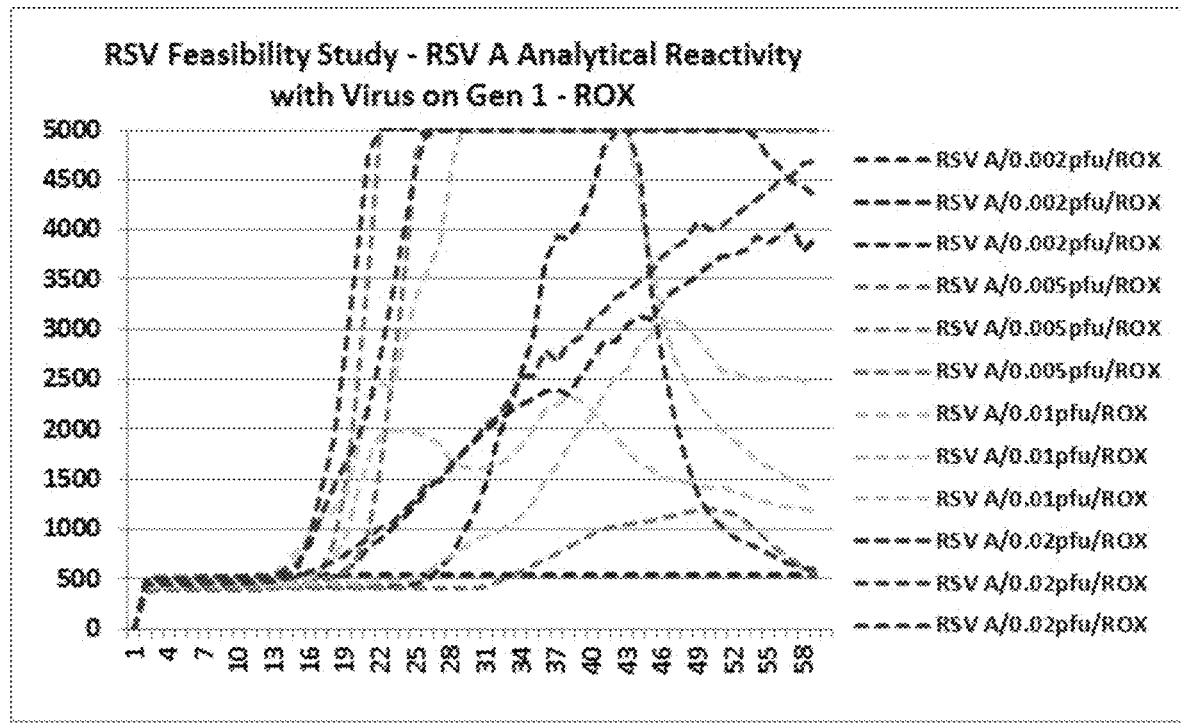

An RSV A analytical reactivity study was undertaken on the Alere™ i instrument using purified viral RNA to assess the sensitivity of the assay. Purified viral RNA was added to pre-heated elution/lysis buffer (pre-heated to 45° C. to mimic a 3-minute pre-heat step), and 100 μl aliquots were immediately transferred to lyophilized reactions to initiate amplification and detection. At each target copy number, triplicate reactions were performed. Fluorescence was monitored in real time. For RSV A, the assay was able to detect 5 copies of purified RNA, but at 2 copies of purified RNA replicates showed ample fluorescence signal above baseline (FIG. 6). These data suggest a sensitivity of 5 copies of purified RNA for the RSV A assay. The assay was able to detect 0.005 pfu of purified virus, while at 0.002 pfu, most replicates were detected above background fluorescence levels (FIG. 7). These data suggest a sensitivity of 0.005 pfu of purified virus for the RSV A assay.

Limit of Detection (Purified virus)—RSV A

Figure 8:
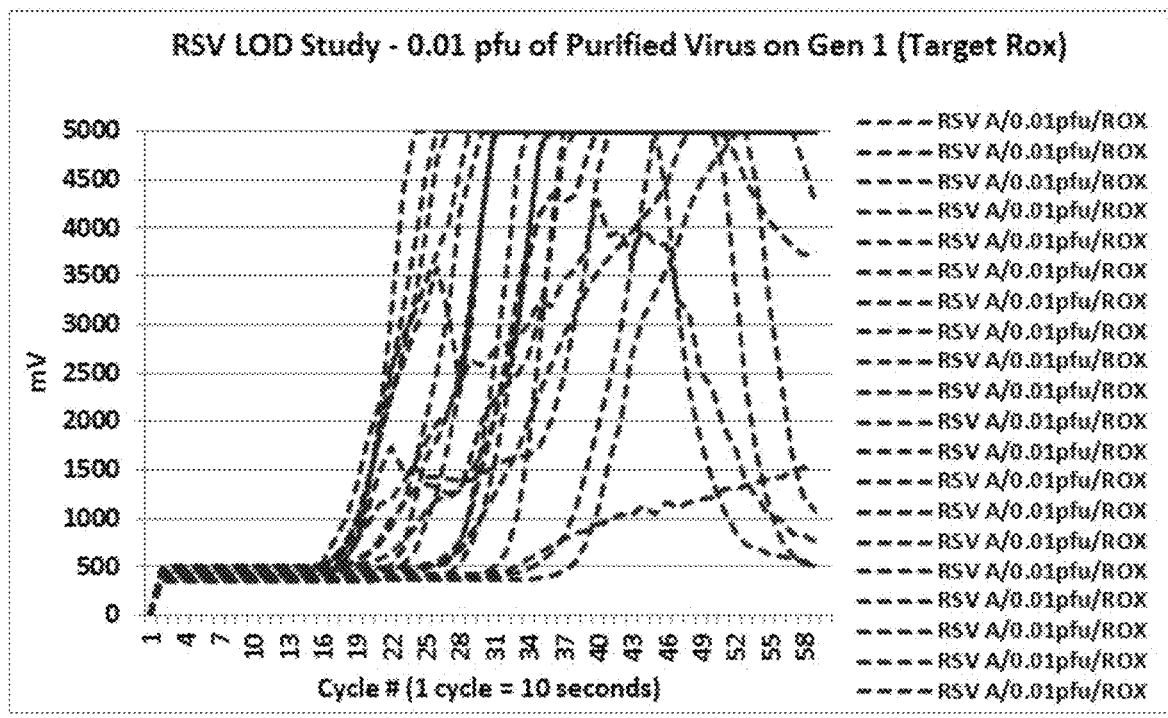
FIG. 8 is a graph showing an exemplary RSV A performed to determine a limit of detection (LOD) with purified virus.

In order to confirm the sensitivity of the RSV A assay, a limit of detection (LOD) study was performed. The study was initiated at 0.005 pfu per reaction (the sensitivity limit as determined during analytical reactivity testing, see section h). The LOD is defined as the lowest target concentration at which 95% of replicates can be detected. The RSV A study began at 0.005 pfu per reaction, but during the 20 replicate study, 2 replicates were not detected as positive so the target concentration was increased to 0.01 pfu (a two-fold increase). At 0.01 pfu, all replicates were detected as positive (FIG. 8), therefore the LOD is 0.01 pfu/reaction of purified viral RNA (strain A2).

Example 4. Analytical Reactivity (Purified RNA) on Alere™ i-RSV B

Figure 9:
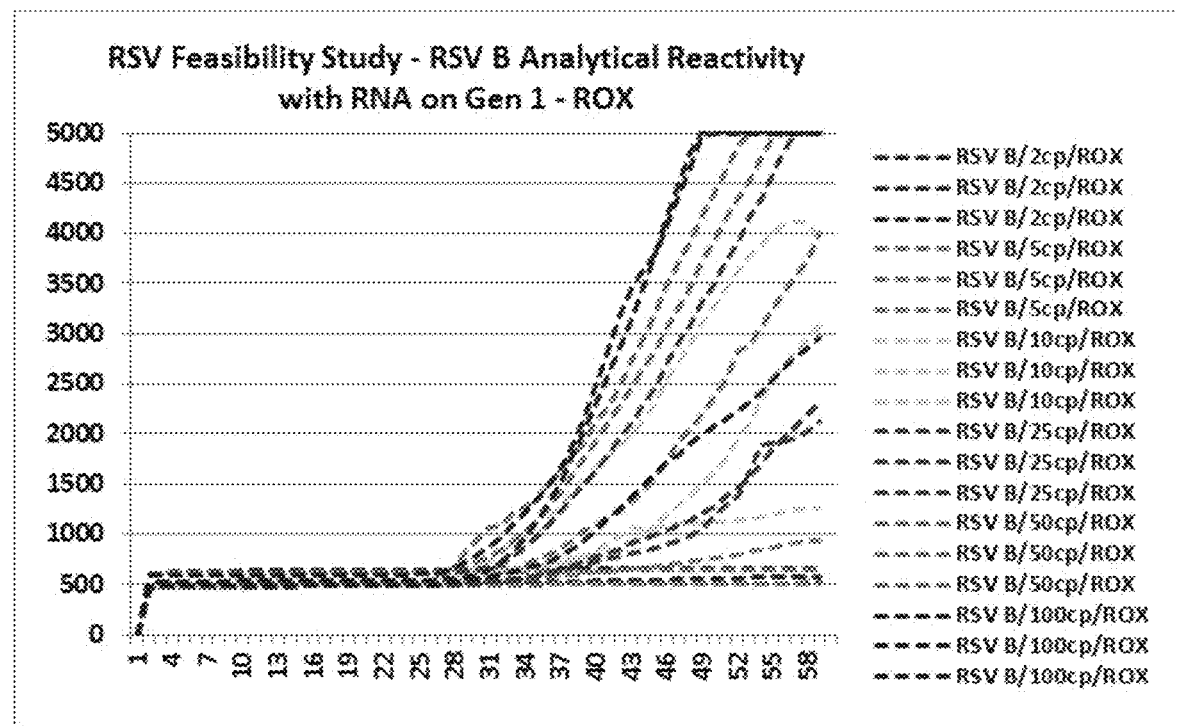
FIG. 9 and FIG. 10 are graphs showing an exemplary RSV B assay showing the assay's reactivity with purified RNA (FIG. 9) and purified virus (FIG. 10). X-axis—cycles (1 cycle=10 seconds); Y-axis—mV.
Figure 10:
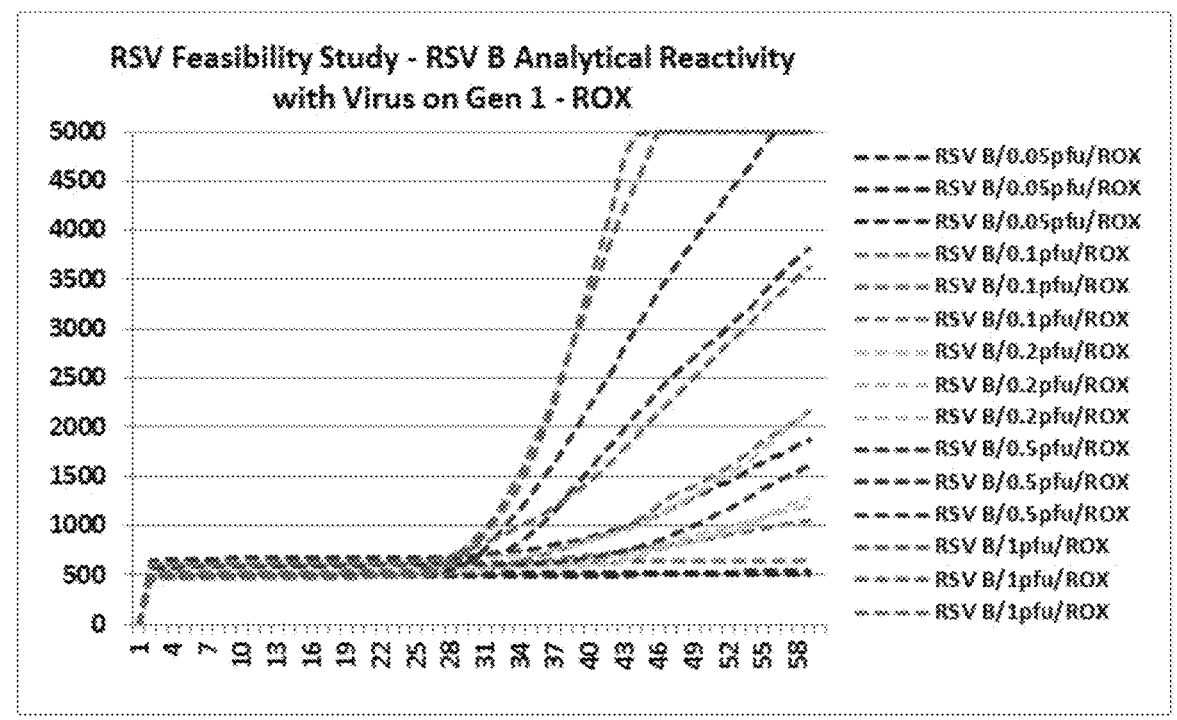
Figure 11:
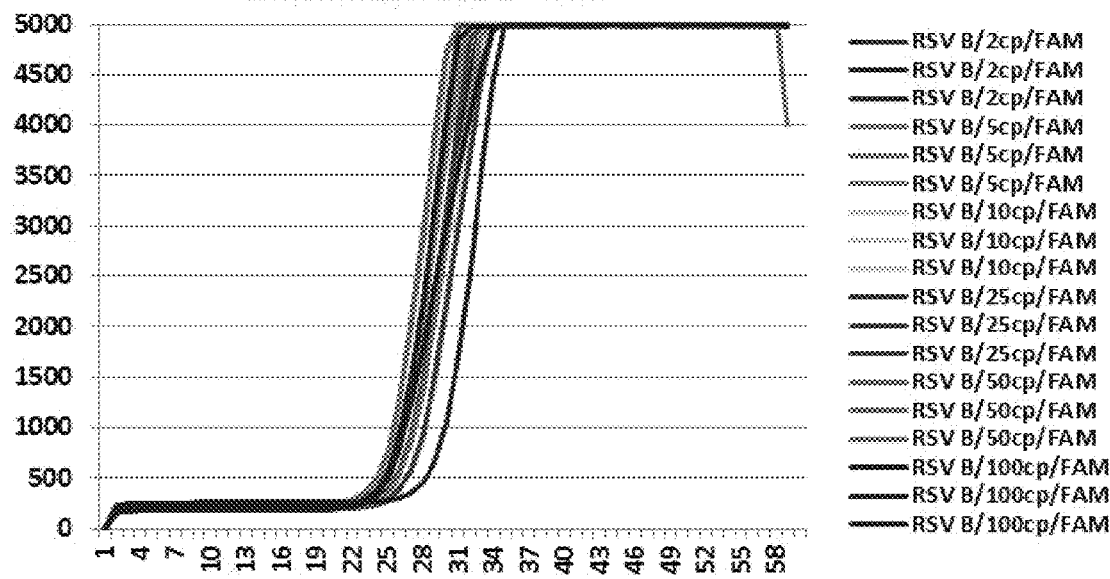
FIG. 11 and FIG. 12 are graphs showing the results of an exemplary RSV B+IC assay performed to determine the assay's reactivity with purified RNA (FIG. 11) and purified virus (FIG. 12).
Figure 12:
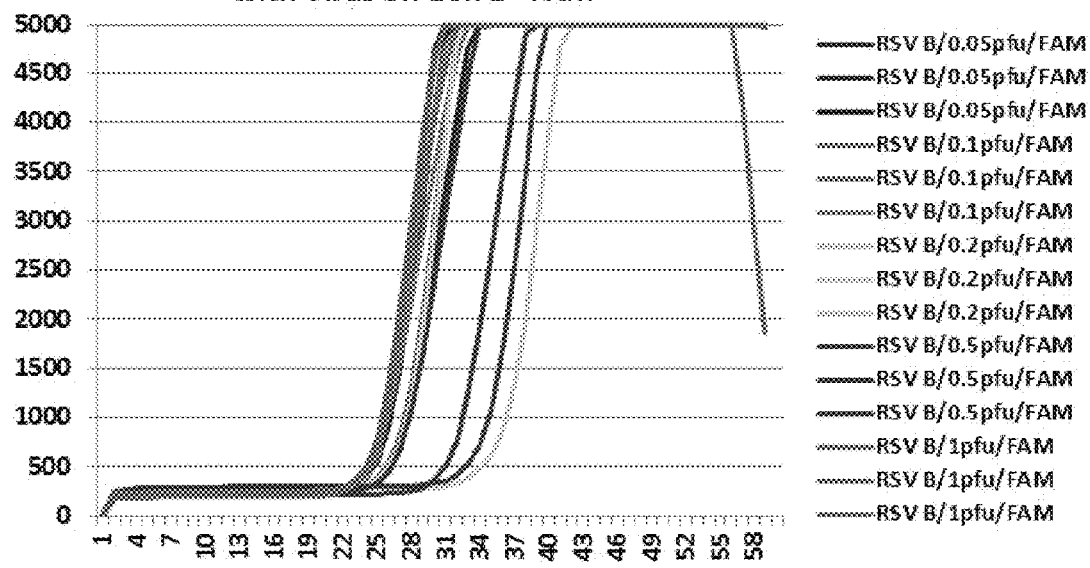

An RSV B analytical reactivity study was undertaken on the Alere™ i instrument using purified viral RNA to assess the sensitivity of the assay. Purified viral RNA was added to pre-heated elution/lysis buffer (pre-heated to 45° C. to mimic a 3-minute pre-heat step), and 100 μl aliquots were immediately transferred to lyophilized reactions to initiate amplification and detection. At each target copy number, triplicate reactions were performed. Fluorescence was monitored in real time. For RSV B, the assay was able to detect 10-25 copies of purified RNA, but at 5 copies of purified RNA, none of the replicates showed ample fluorescence signal above baseline (FIG. 9). These data suggest a sensitivity of 10-25 copies of purified RNA for the RSV B assay. In FIG. 10, the assay was able to detect 0.02-0.05 pfu of purified virus; at 0.02 pfu all three replicates showed weak fluorescence signal, while at 0.01 pfu, most replicates were detected above baseline fluorescence levels. These data suggest a sensitivity of 0.02-0.05 pfu of purified virus for the RSV B assay. IC performance was also assessed during this study, and in all instances provided robust amplification/detection, with saturated signal for all replicates (FIGS. 11-12)

Limit of Detection (Purified Virus) on Alere™ i—RSV B

Figure 13:
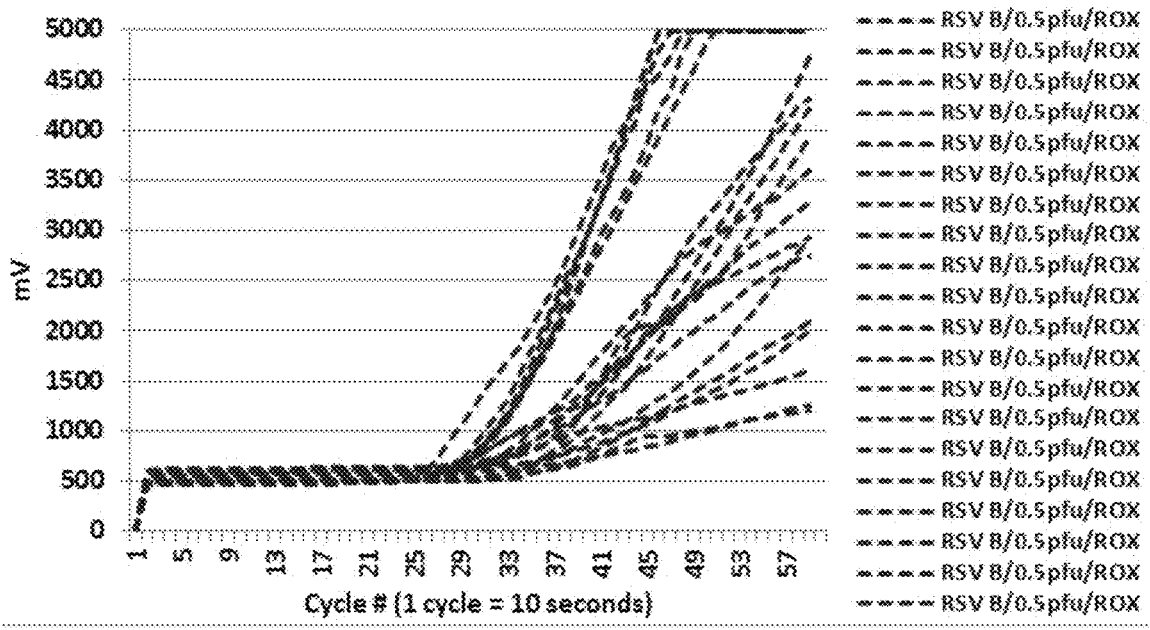
FIG. 13 and FIG. 14 are graphs showing the results of an exemplary assay performed to determine a limit of detection (LOD) with purified virus of RSV B performance (FIG. 13) and RSV B+IC performance (FIG. 14).
Figure 14:
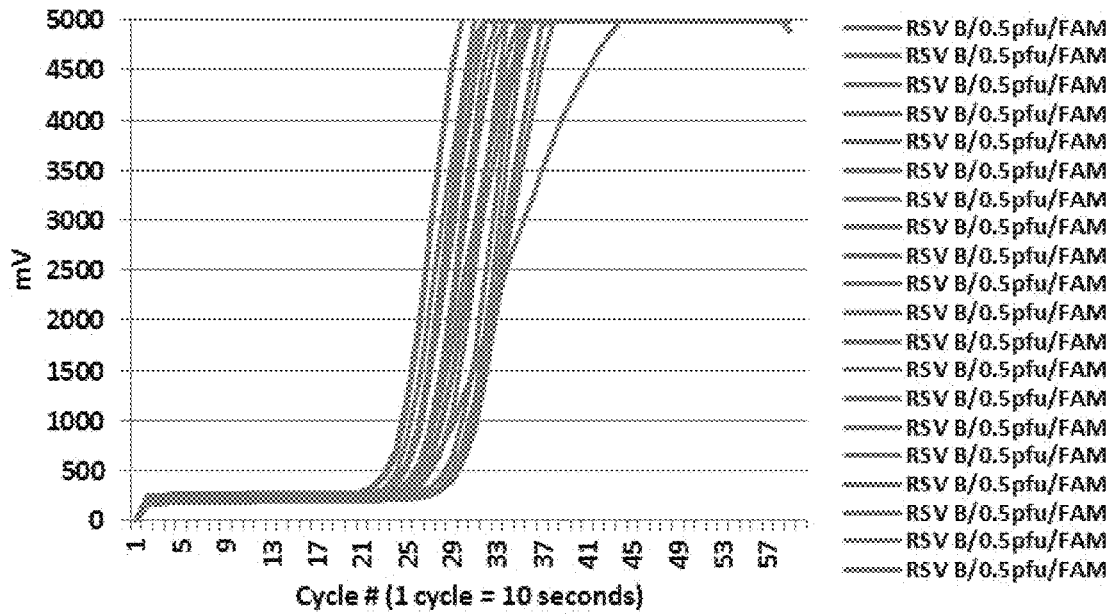

In order to confirm the sensitivity of the RSV B assay, a limit of detection (LOD) study was performed. The study was initiated at 0.05 pfu per reaction (the sensitivity limit as determined during analytical reactivity testing, see section h). The LOD is defined as the lowest target concentration at which 19/20 replicates (95%) can be detected. At 0.05 pfu per reaction, 20/20 replicates were detected as positive (FIG. 13), therefore the LOD is 0.05 pfu/reaction of purified viral RNA (strain B1). IC performance was also assessed during this study, and in all instances provided robust amplification/detection, with saturated signal for all replicates (FIG. 14).

Example 5. NTC Reproducibility

Figure 15:
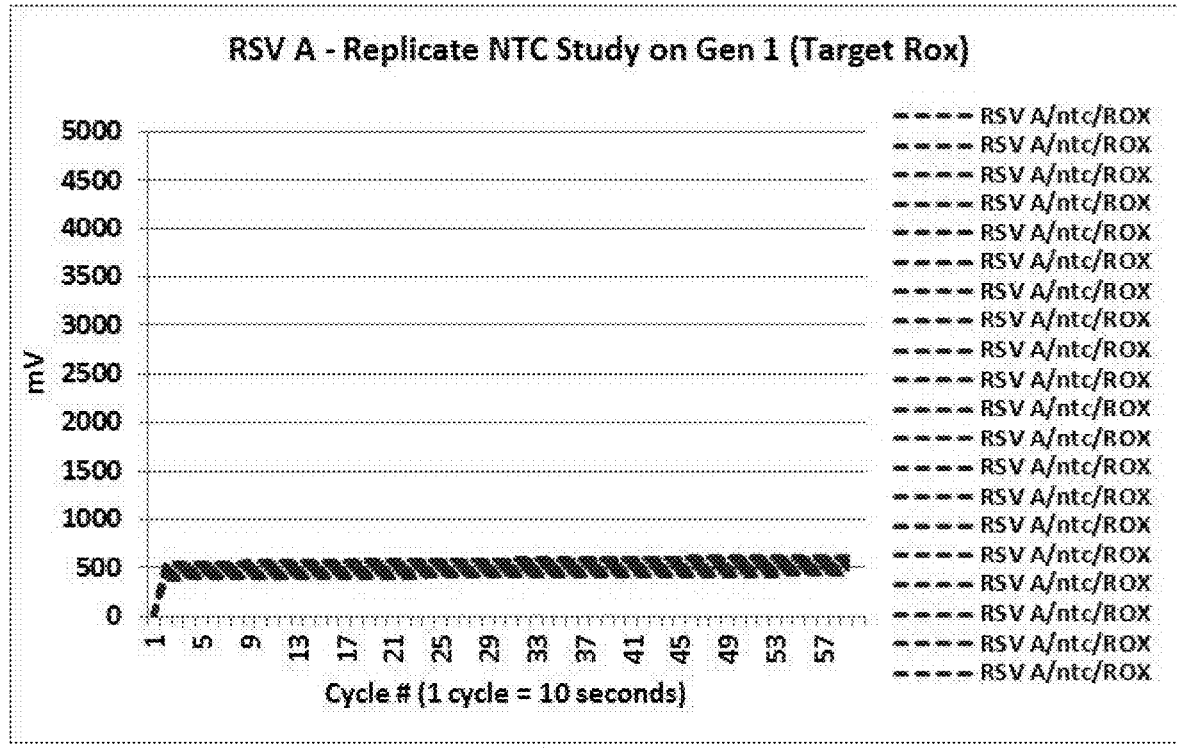
FIG. 15-17 are graphs showing the results of a "no target copies" (NTC) replicate study of RSV A assay (FIG. 15), RSV B assay (FIG. 16), and RSV B+IC assay (FIG. 17) to determine whether the assays would generate false positive results when no target was present in the reaction. X-axis—cycles (1 cycle=10 seconds); Y-axis—mV.
Figure 16:
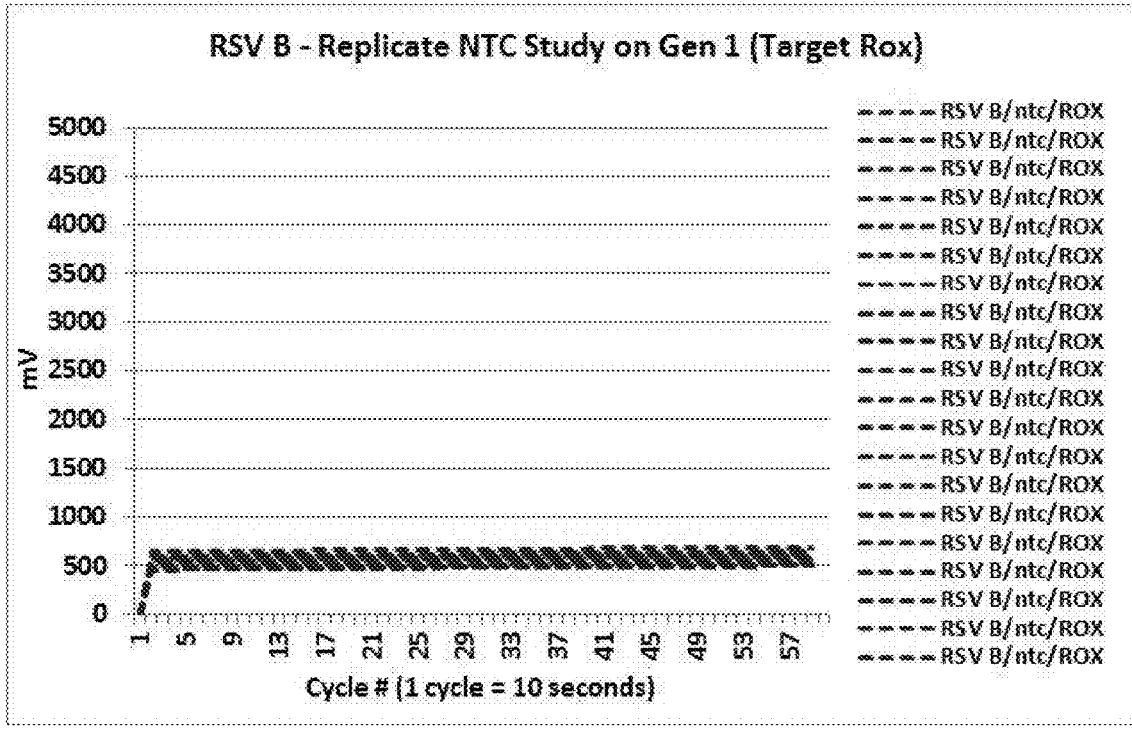
Figure 17:
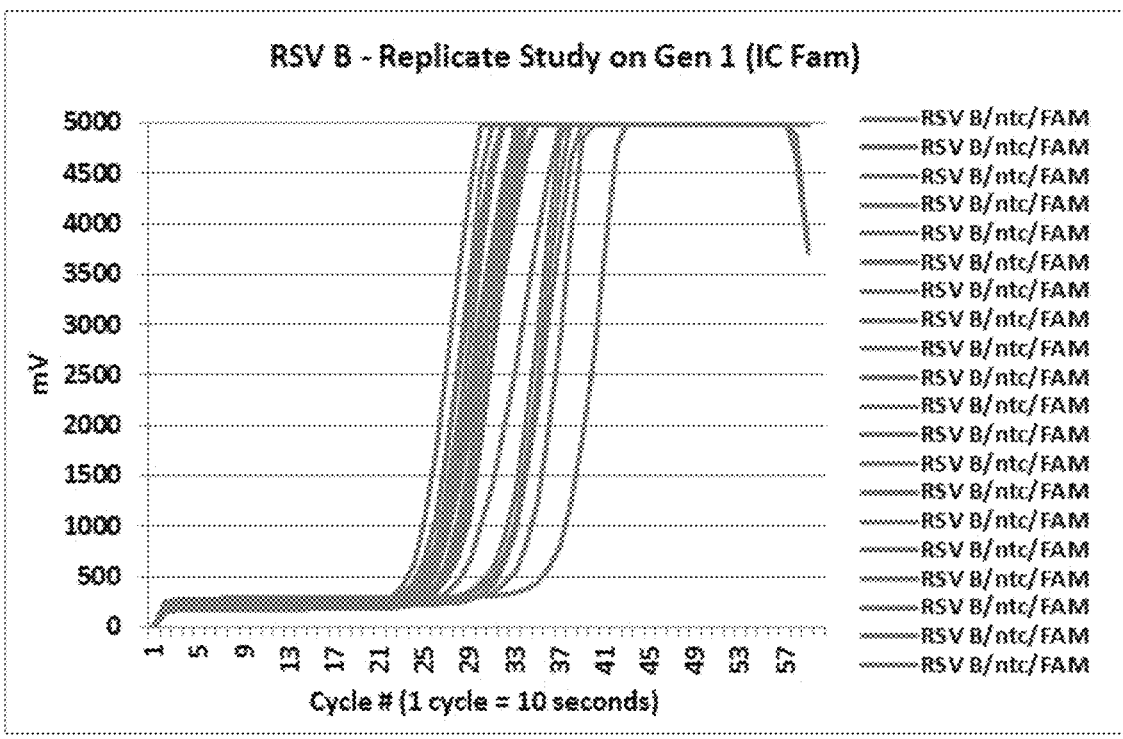

To confirm that the RSV A and RSV B assays do not generate false positive results when RSV target is not present in the respective reactions, a NTC replicate study was performed. For each assay, twenty NTC reactions were screened on the Alere™ i instrument, as fluorescence was monitored in real time to determine whether any increase above background fluorescence levels was observed. In FIG. 15, results for RSV A are shown, and in FIG. 16 and FIG. 17 the results for the RSV B and IC assays are depicted, respectively. Both the RSV A and RSV B assays failed to show any false positives, indicating that the assays are stable and that false positives are not to be an expected issue moving forward. The data also show the reproducibility of the IC system as all replicates showed strong (saturated) IC amplification and detection.

Inclusivity

Figure 18:
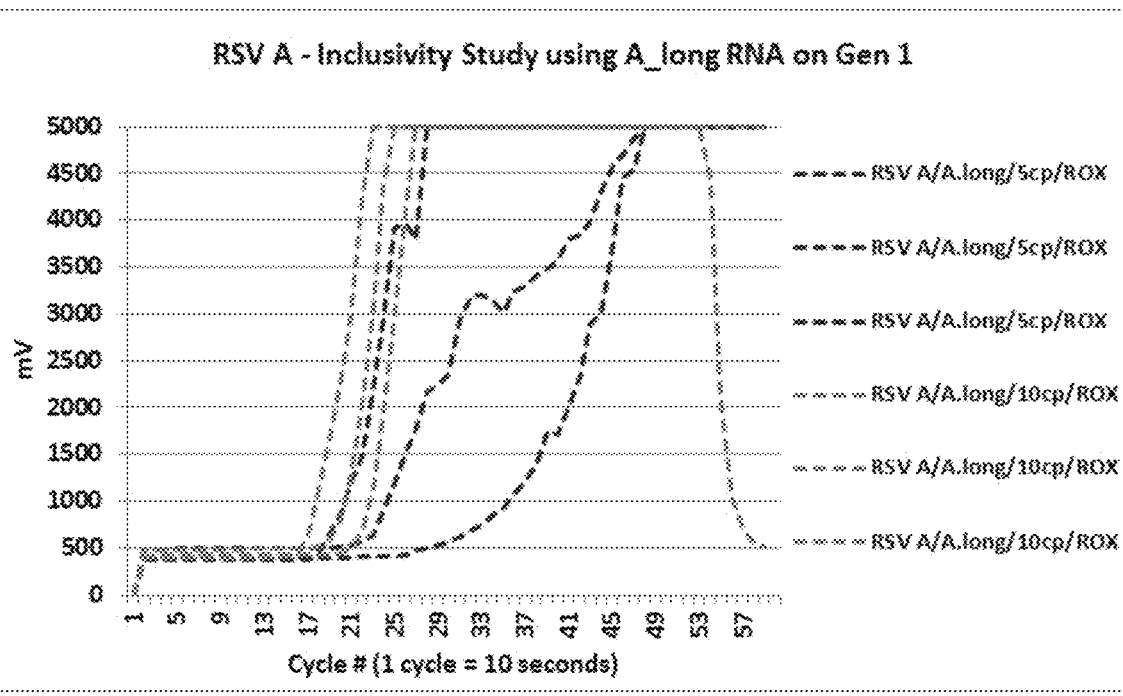
FIG. 18 and FIG. 19 are graphs showing the results of an exemplary inclusivity study of RSV A assay (FIG. 18) and RSV B assay (FIG. 19) to determine whether the assays provide a similar level of performance across multiple strains (A2 was used as the development strain, shown are the results with A long). The strain A Long was screened at either 5 copies (determined to be the LOD for development strain A2) or 10 copies of purified RNA per reaction, in triplicate. (Rox—target detection; Fam—internal control detection).
Figure 19:
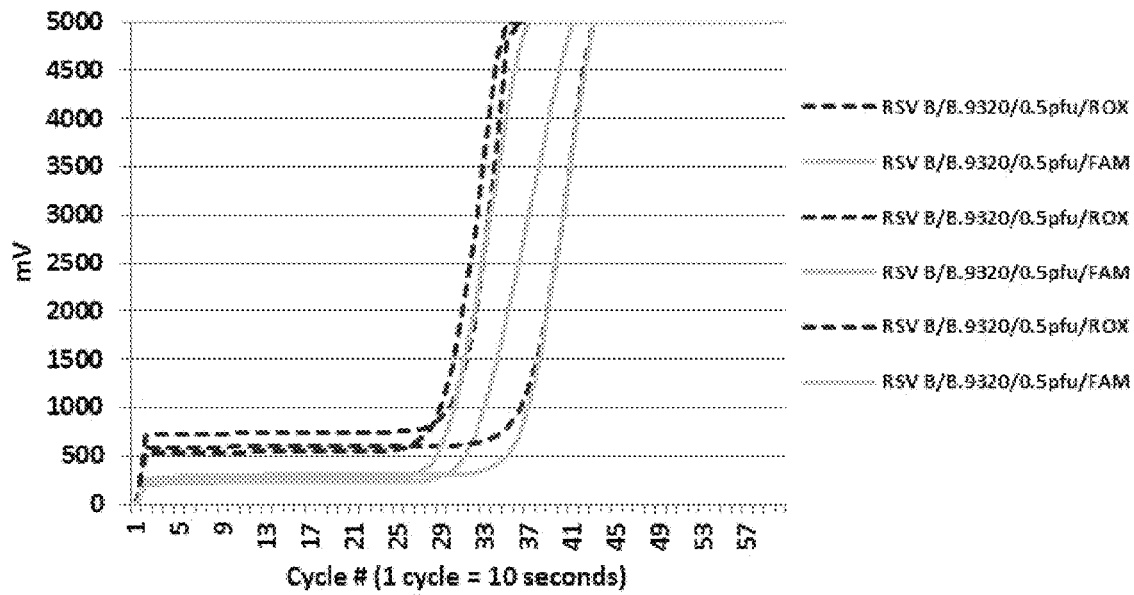

The RSV A and RSV B assays were developed using the RSV strains A2 and B1, respectively. These strains are commercially available as purified virus or purified RNA, making them suitable and convenient for development work. To ensure that the RSV A and RSV B assays worked on strains other than the development strains, additional RSV strains were purchased and tested. For RSV A, the LOD was determined to be 5 copies of purified RNA when using the development strain A2. The strain A Long was also tested at 5 copies of purified RNA, confirming that detection at this target copy number is robust, suggesting that the RSV A assay can work across RSV A strains (FIG. 18). For RSV B, the LOD was determined to be 0.5 pfu of purified virus when using the development strain B1. The strains B 9320 and B 18537 were also screened at 0.5 pfu of purified virus, and the data confirm that detection at this target copy number is robust, suggesting that the RSV B assay can work across multiple RSV B strains (FIG. 19).

Example 6. Cross-Reactivity

Figure 20A:
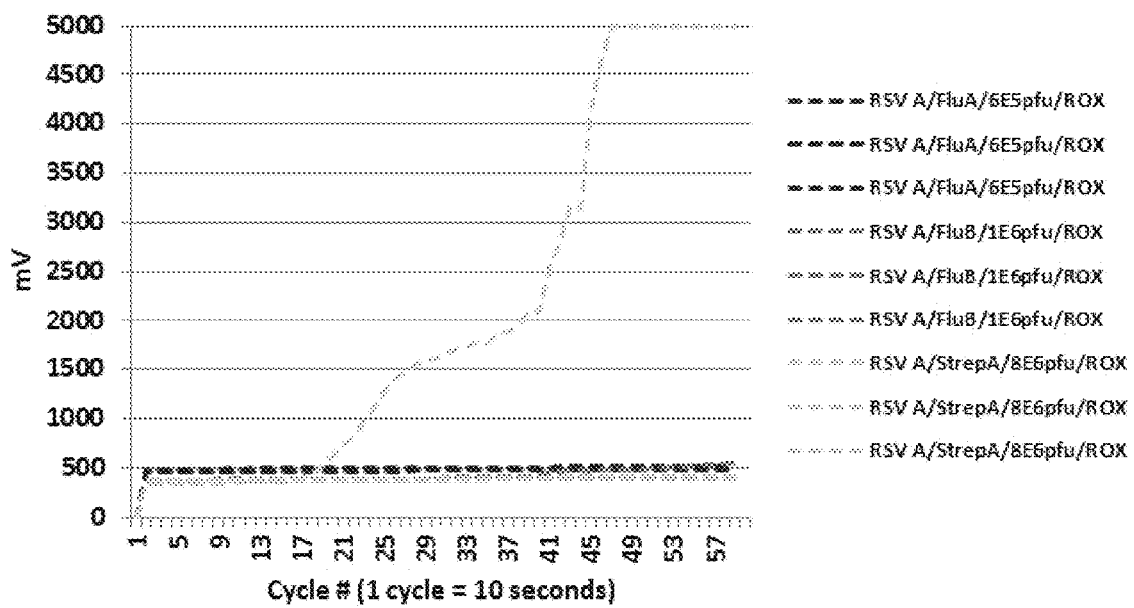
FIG. 20A-B are graphs showing the results of an exemplary cross-reactivity study to determine whether the RSV A assay (FIG. 20A) and RSV B (FIG. 20B) would provide specificity against non-RSV species.
Figure 20B:
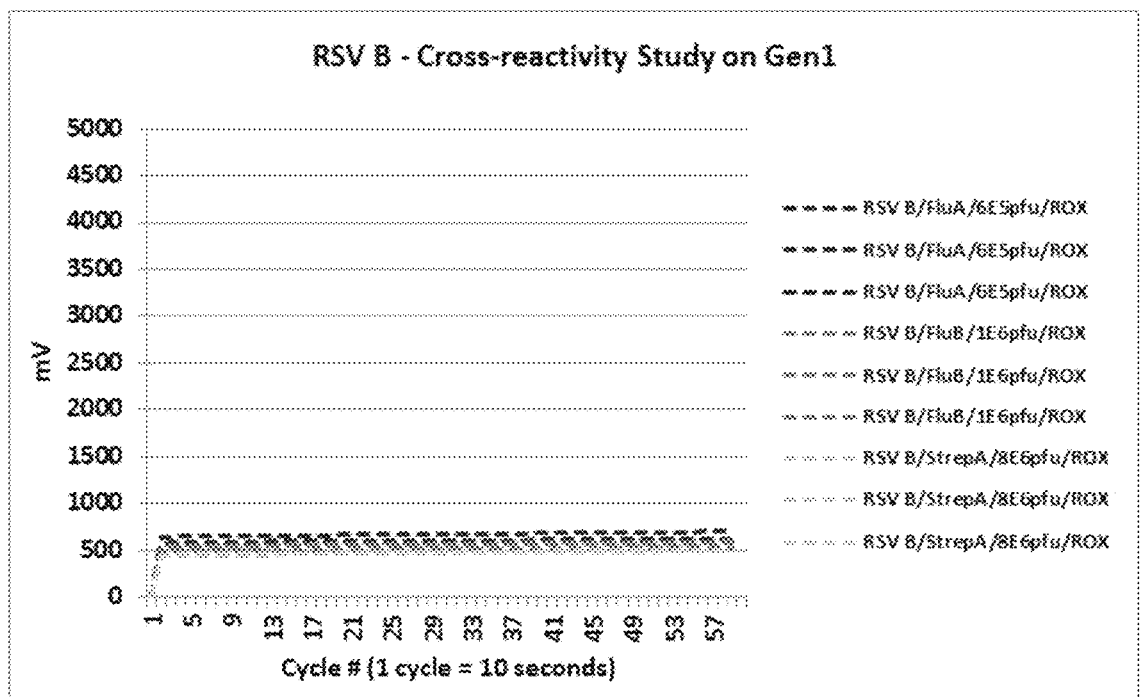

To ensure that the RSV A and B assays each provide specificity for RSV, a series of cross-reactivity experiments were performed using common respiratory infectious agents. Influenza A virus, Influenza B virus and Strep A bacteria (common respiratory disease infectious agents), were screened at high target concentrations. The concentration of each target used was purposefully high to mimic a worst case scenario, and the final concentration per reaction was determined based on adding 2 µl of the stock material to each reaction. RSV A and B assays were screened with Influenza A virus at 6e5 pfu/reaction, Influenza B virus at 1e6 pfu/reaction and Strep A at 8e6 pfu/reaction. The concentration of each target used was purposefully high to mimic a worst case scenario, and the final concentration per reaction was determined based on adding 2 µl of the stock material to each reaction. Each target was tested in triplicate reactions, and the results are shown in FIGS. 20A-B. The RSV A or RSV B assays did not detect Influenza A, Influenza B or Strep A, indicating that these assays provide good specificity against non-RSV species. For RSV A, one replicate of Strep A showed a saturated fluorescence signal. This sample was subsequently analyzed by ESI-MS which confirmed the reaction was contaminated with RSV target/amplicon as the product generated was the expected product generated from amplification off of the RSV genome (this sequence does not exist in the Strep A genome).

Figure 21A:
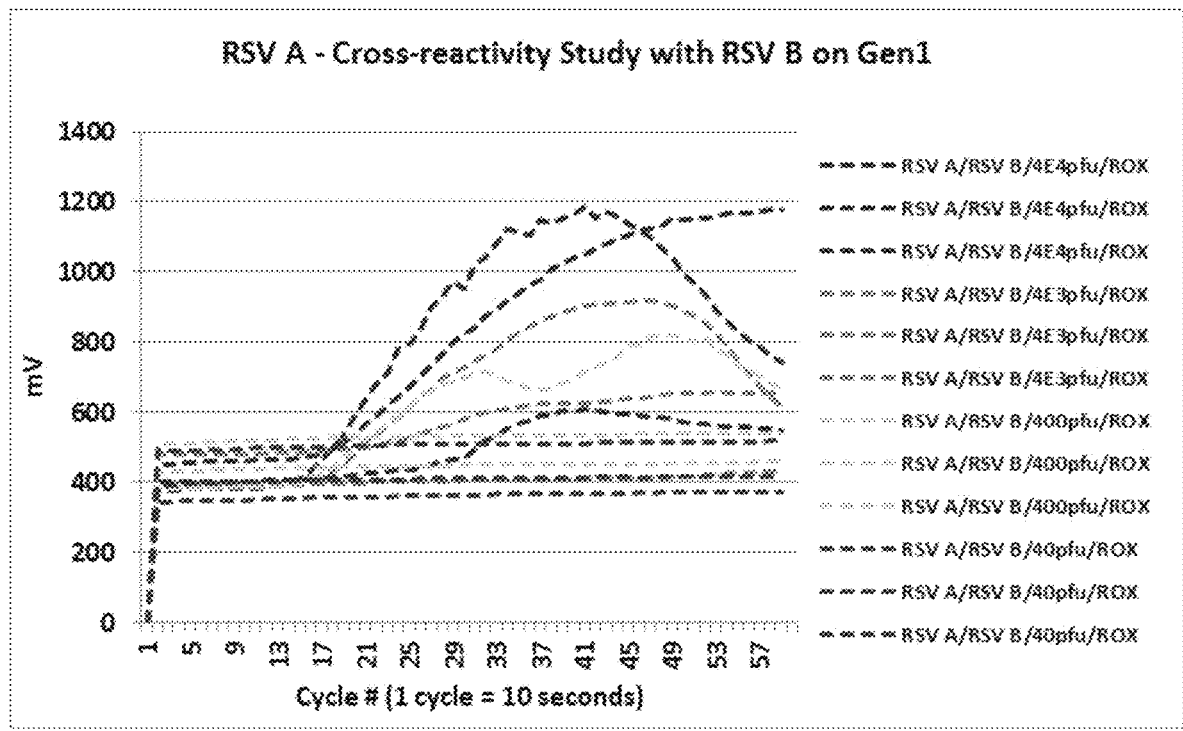
FIG. 21A-B are graphs showing the results of an exemplary cross-reactivity study to determine whether the assay would provide specificity against opposite RSV subtypes. The RSV A assay was screened against RSV B target (FIG. 21A), and the RSV B assay was screened against RSV A target (FIG. 21B).
Figures 21B, 22, 23:
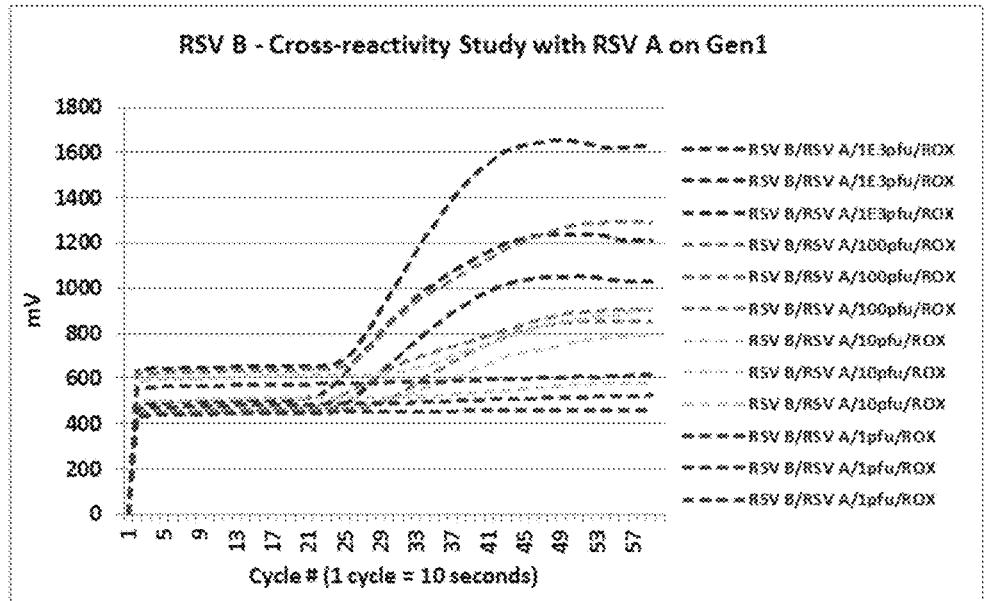
FIG. 22 and FIG. 23 are graphs showing BLAST analyses performed using the RSV A product 1 sequence against RSV B sequences (FIG. 22), and RSV B product 1 sequence against RSV A sequences (FIG. 23).
Representative "top hits" are shown aligned to the RSV A template, molecular beacon and product sequences, along with representative RSV A strain sequences and representative "top hits" are shown aligned to the RSV B template, molecular beacon and product sequences, along with representative RSV B strain sequences, respectively. BLAST analyses were carried out at blast.ncbi.nlm.nih.gov/Blast.cgi, using the Basic BLAST 'nucleotide blast' program (BLASTN 2.2.30+), the Nucleotide collection (nr/nt) database, specifically targeting RSV type B (taxid: 208895), and RSV type A (taxid: 208893 & 1439707), respectively, with standard BLAST parameters adjusted to searching short input sequences. Sequences in FIG. 22 are provided in the sequence listing as SEQ ID NOs: 1, 4, 4, 15, 16, 17, 18, 19, 17, 20, 21, and 22, respectively, as shown from top to bottom in FIG. 22. Sequences in FIG. 23 are provided in the sequence listing as SEQ ID NOs: 6, 11, 11, 23, 24, and 25, respectively, as shown from top to bottom in FIG. 23.

In addition to testing the RSV assays against non-RSV species for confirmation of specificity, the RSV A assay was screened against RSV B target, and the RSV B assay was screened against RSV A target. The RSV A and B target sequences are similar to one another, and some level of cross-reactivity was expected. As shown in FIG. 21A, when the RSV A assay is challenged with RSV B virus, the assay does detect it, although the sensitivity is greatly diminished as compared to detection of RSV A virus. The RSV A assay has an LOD of 0.01 pfu/reaction for RSV A target, while in this study the RSV A assay could only detect down to between 400-4,000 pfu/reaction of RSV B target. Similarly, when the RSV B assay is challenged with RSV A virus, the assay detects it, but once again, at a diminished sensitivity as compared to RSV B virus (FIG. 21B). The RSV B assay has a LOD of 0.5 pfu/reaction for RSV B target, but was only able to detect between 10-100 pfu/reaction of RSV A target.

Shown in FIGS. 22 and 23 are alignments between the template and molecular beacon components of the RSV A assay and RSV A and RSV B targets (FIG. 22), as well as the RSV B assay components against RSV B and RSV A targets (FIG. 23). As can be seen from the alignments, there is significant homology between the RSV A target sequence and genomic sequence from a subset of RSV B strains. Shown are several strains with significant homology to the RSV A target sequence (E values<1e-04, representing the top 24 hits from the top 200 list). From BLAST analysis, no other RSV B strains showed significant homology to RSV A target sequence (the remaining top 200 hits (25 through 200) all generated E values of >1). The top RSV B hits certainly provide enough homology to generate some level of amplification and detection of RSV B when using RSV A reagents.

As with the RSV A assay and RSV B target, there is significant homology between the RSV B assay and the genomic sequence of RSV A. Shown in FIG. 23 is a representative RSV A strain aligned with the RSV B assay templates, molecular beacon and product sequences. This RSV A strain is identical to the top 200 RSV A BLAST hits (all hits have an E value of 3e-08), indicating that the RSV A genomic sequence has very high homology for the RSV B assay target sequence, suggesting amplification off of the RSV B genome will occur to some extent.

Example 7. Assay Performance in Presence of Clinical Matrix

Figure 24:
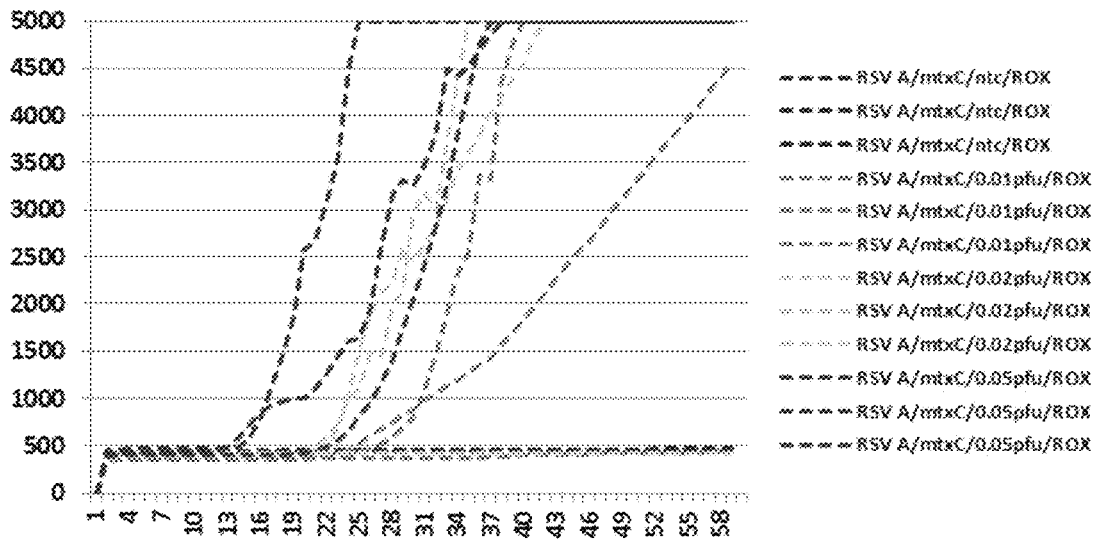
FIG. 24 and FIG. 25 are graphs showing the results of an exemplary experiment performed to assess the performance of RSV A lyophilized reagents (FIG. 24) and RSV B lyophilized reagents (FIG. 25) in the presence of clinical matrix. Both assays were screened with anonymous donor swab pool C.

To provide an indication as to RSV A and B assay performance when tested in the presence of clinical matrix, a series of anonymous donor swabs were tested as pooled samples. Three pools were generated, A, B & C, each consisting of 4 individual anonymous donor swabs, respectively. Each swab was eluted in 2.5 ml of pre-heated (3 minutes) elution/lysis buffer, by swirling the swab for 10 seconds and expressing prior to removing from the buffer. The swab eluates were then combined to make pools of 10 ml each. The RSV A and B assays were first initially screened using LOD virus concentrations, and virus concentrations were increased until ⅔ replicates generated 'positive' results. The data indicate that clinical matrix can impact assay performance, and the impact varies greatly. The RSV A assay was unable to detect 0.01 pfu/reaction (the assay's LOD without clinical matrix present) when challenged with pool A, but a doubling of the pfu/reaction to 0.02 generated good amplification and detection in a reproducible fashion. Matrix pool B provided the least inhibition, as the RSV A assay readily detected all replicates at 0.01 pfu/reaction. As depicted in FIG. 24, RSV A assay screened with anonymous donor swab pool C, was the most inhibitory pool and required the addition of 0.05 pfu/reaction (5-fold above the assay's LOD) to generate consistent positive results.

Figure 25:
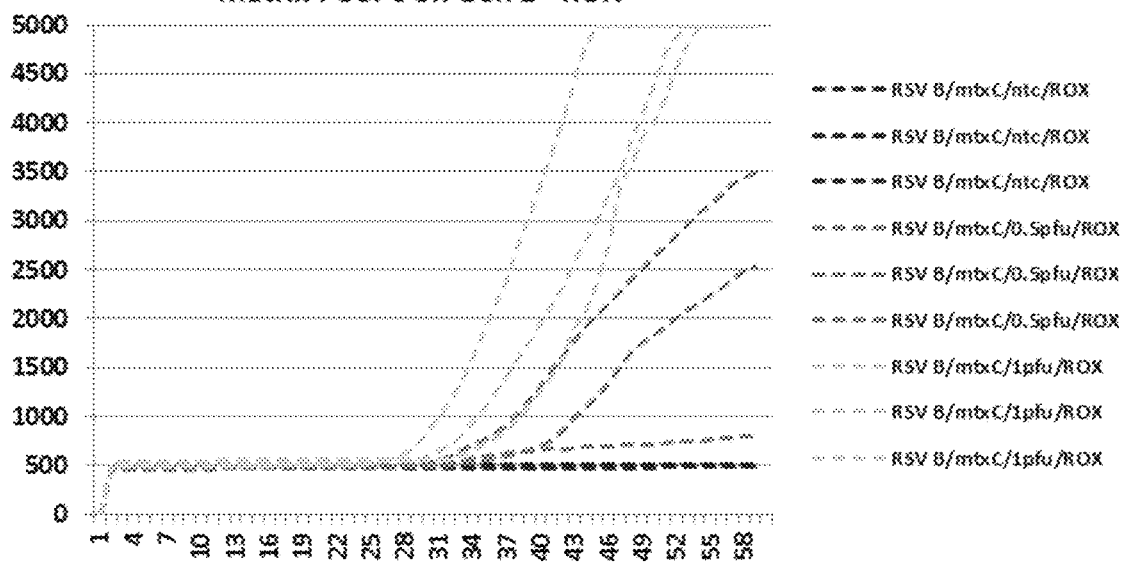
Figure 26:
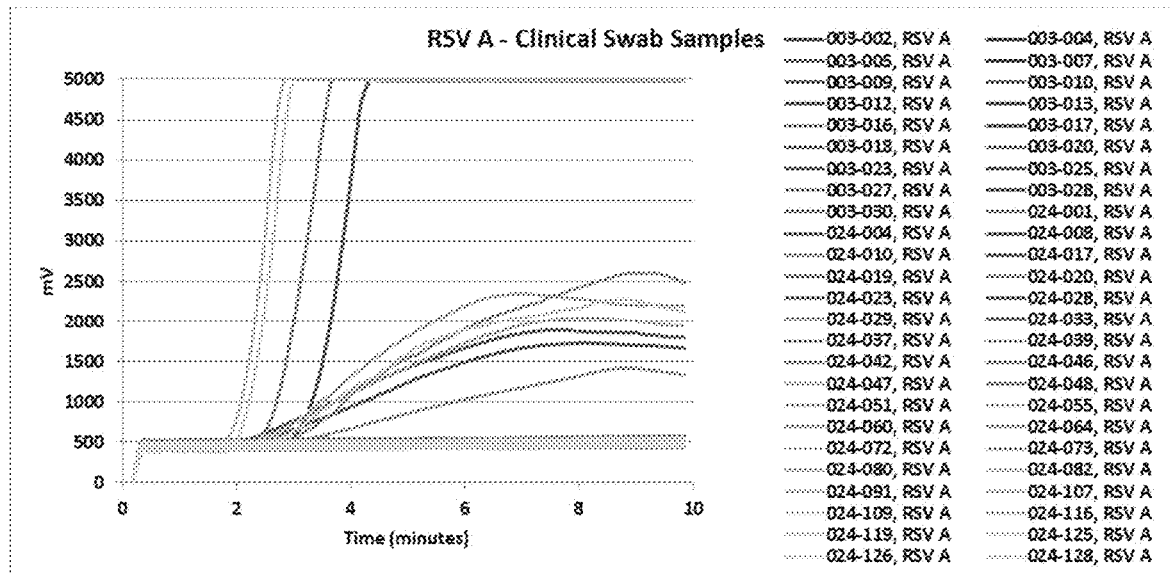
FIG. 26-28 are graphs showing the summary results of a RSV A NEAR assay (FIG. 26), a RSV B NEAR assay (FIG. 27), and a RSV B+IC NEAR assay (FIG. 28) of 50 clinical swab samples.
Figure 27:
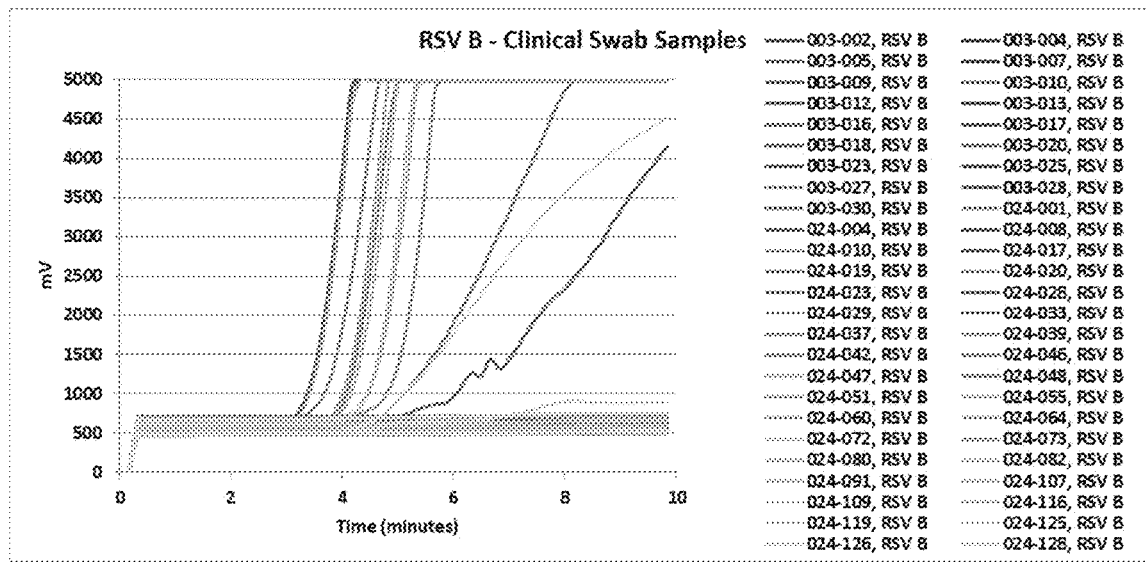
Figure 28:
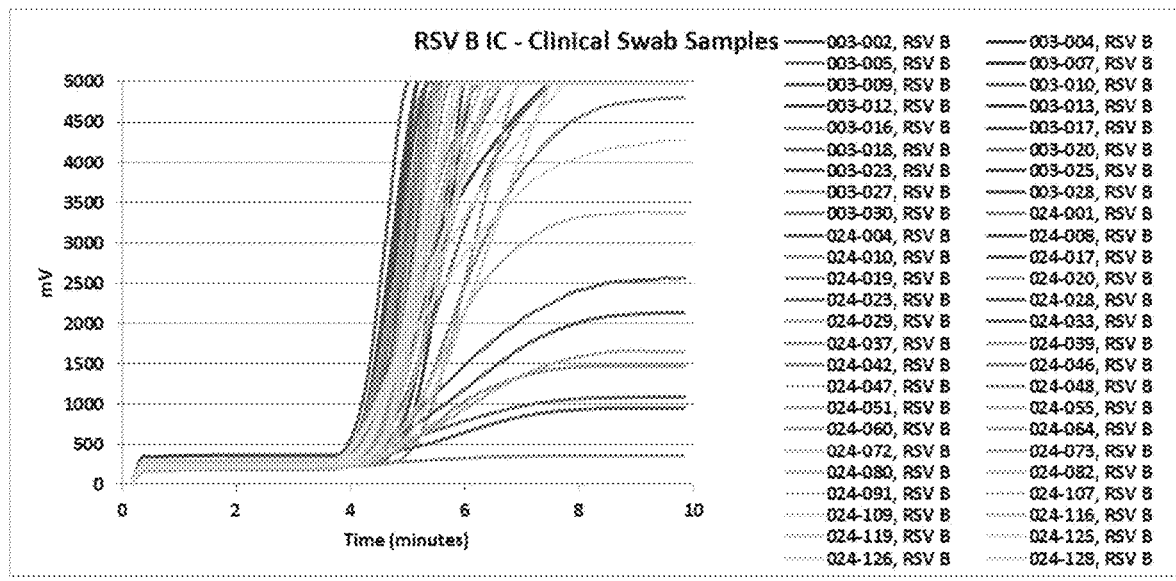
Figure 29:
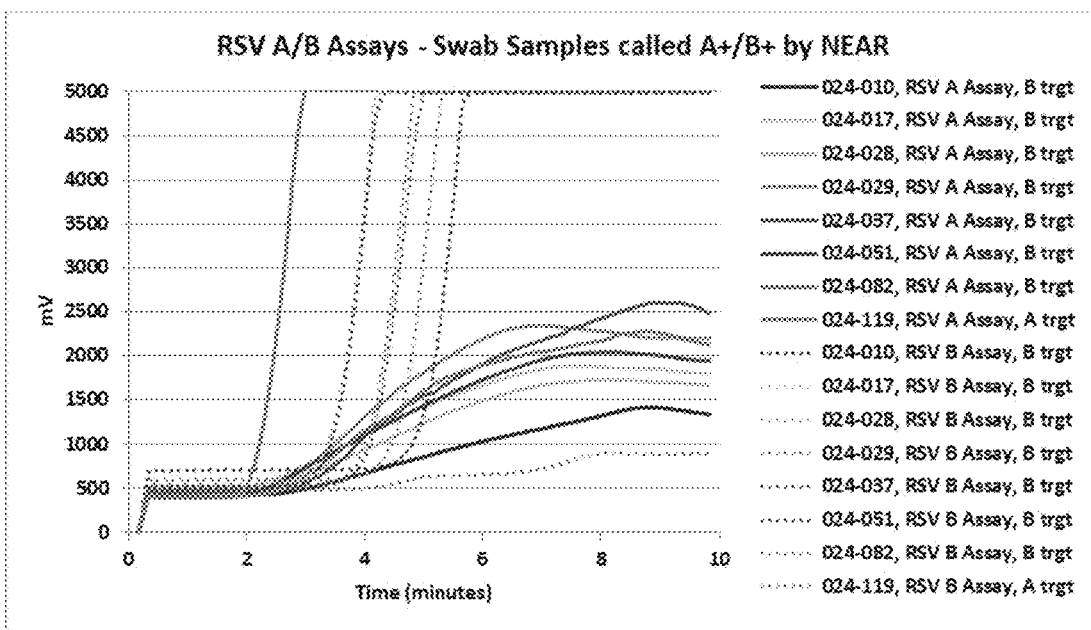
FIG. 29 shows exemplary results depicting the real time fluorescence curves for the subset of clinical swab samples that were called positive using the RSV A & B NEAR assays.
Figure 30:
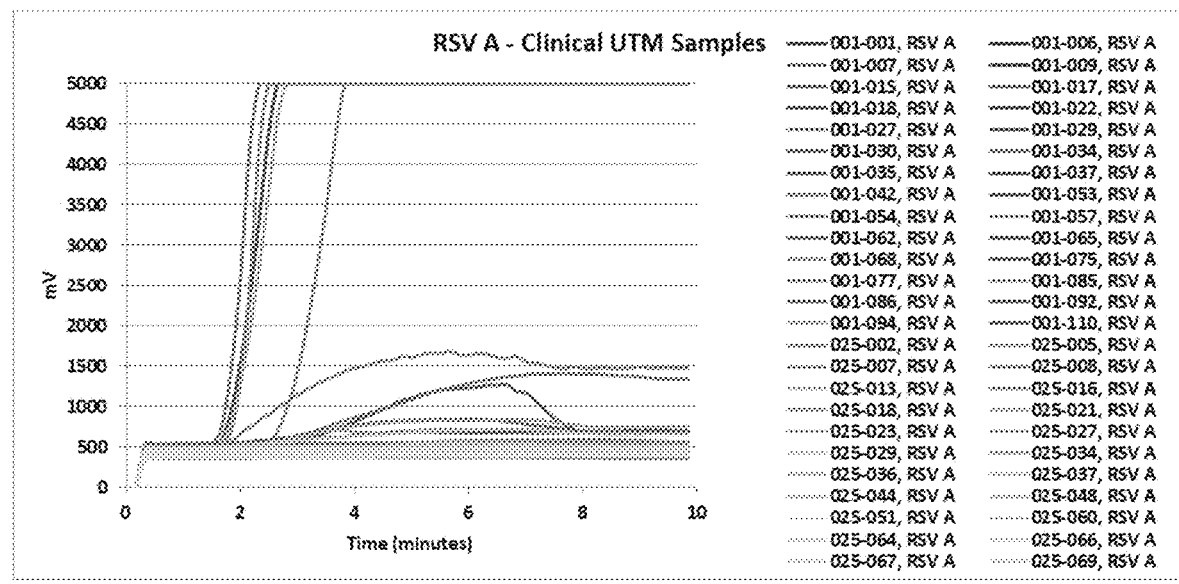
FIG. 30-32 shows exemplary results depicting the real time fluorescence curves for the 50 clinical UTM samples that were screened using the RSV A NEAR assay (FIG. 30), RSV B NEAR assay (FIG. 31), and RSV B+IC NEAR assay (FIG. 32).
Figure 31:
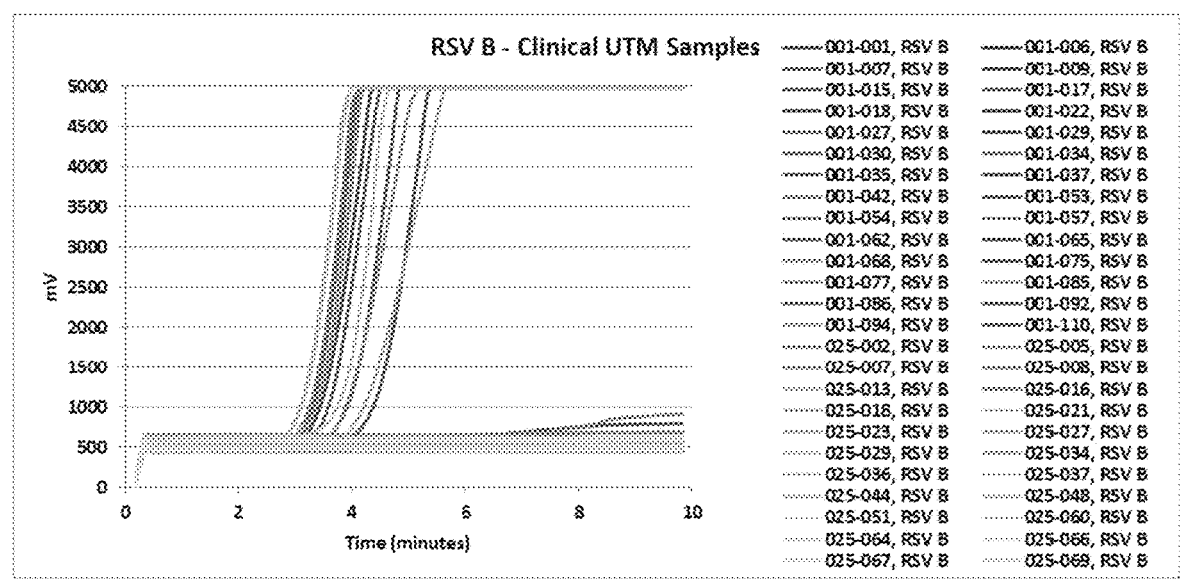
Figure 32:
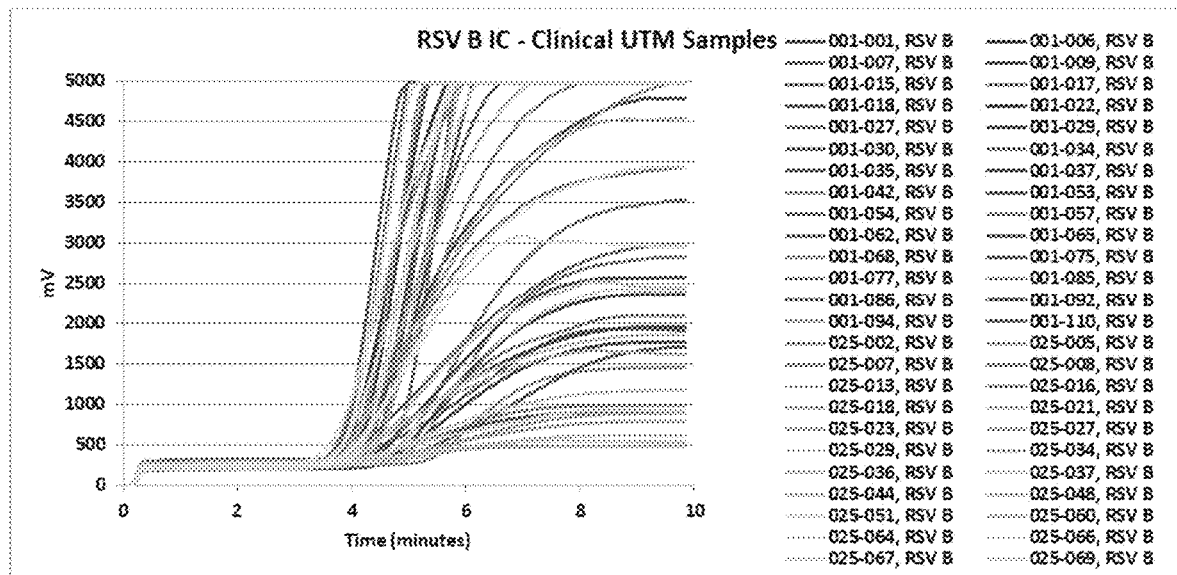
Figure 33:
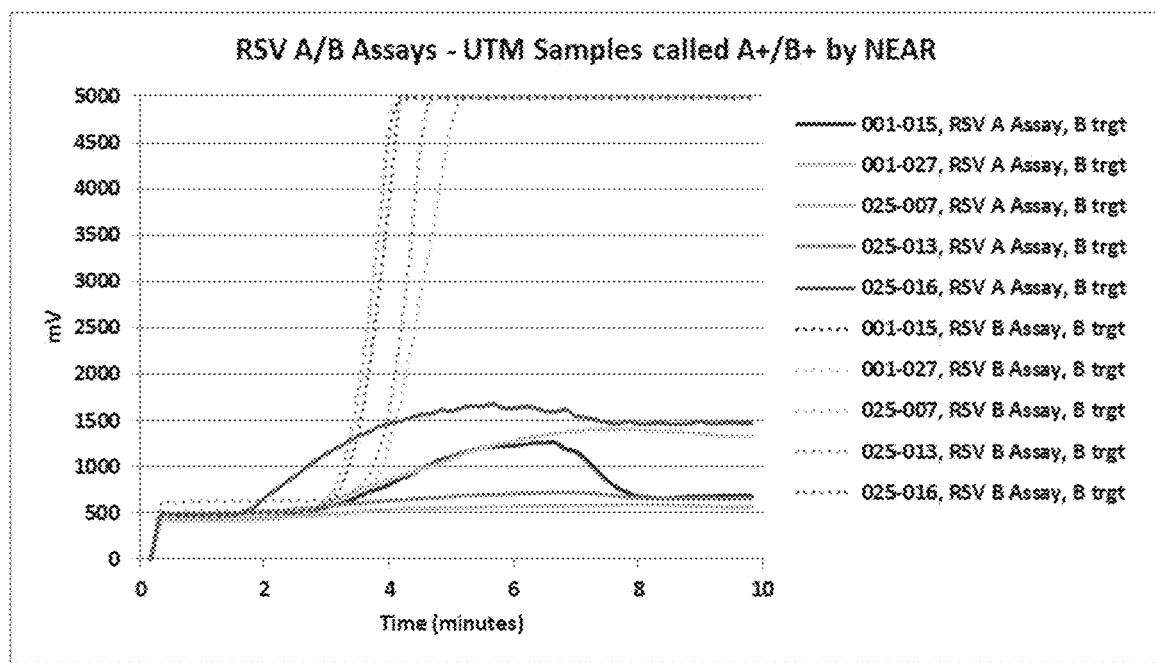
FIG. 33 shows exemplary results depicting the real time fluorescence curves for the subset of clinical UTM samples that were called positive using the RSV A & B NEAR assays.

Although the RSV B assay was able to detect 0.5 pfu/reaction (the assay's LOD without clinical matrix present) when challenged with pools A, B & C, amplification and detection was not strong (FIG. 25). Matrix pool A was the most inhibitory pool, with only some replicates showing fluorescence signal above background, and other replicates showing weak signal. For each of the three matrix pools tested, increasing the target concentration to 1 pfu/reaction resulted in strong amplification and detection, with all replicates generating saturated fluorescence signal (2-fold above assay's LOD).

A RNaseP qPCR assay was used to quantitate the amount of human gDNA present in each matrix pool. The qPCR data suggest that per 100 µl sample of matrix A, B & C contain 4.6 ng, 5.0 ng and 4.9 ng of human gDNA, respectively. These concentrations should not be inhibitory to the RSV A, B or IC assays, as the assays were shown to work well when challenged with concentrations similar to those in the pools in Example 2. The RNase and DNase levels of each pool were also determined, qualitatively, using IDT's RNase Alert and DNase Alert kits. The three pools showed very low DNase levels but all three pools retained significant RNase activity, with pool B showing the greatest activity (data not shown). The significant level of RNase activity found in each pool is believed to be a major contributor to the reduced assay performance, as shown in FIGS. 22 and 23, where the target input had to be increased over each assay's LOD to provide good amplification and detection.

Example 8. Clinical Sample Study

In an effort to determine how well the RSV A, RSV B and IC assays would perform against clinical samples, 50 direct clinical swab samples that were stored frozen at −80° C., and 50 UTM samples that were also stored frozen at −80° C. were used. The samples were not characterized, meaning it was unknown which, if any, samples were positive for RSV. As part of this study, the RSV A & B tests were performed on the clinical samples, and further characterized by performing RSV qPCR (used as the 'gold standard', to determine RSV +/− status and copy number if appropriate), RNaseP qPCR (to determine the human gDNA content) and RNase/DNase nuclease testing (to determine the levels of RNase and DNase activity).

Briefly, the RSV A & B NEAR assays were screened by first either eluting each swab sample in 2.5 ml of pre-heated elution/lysis buffer by dipping the swab into the buffer, swirling for approximately 10 seconds, expressing the swab and then removing the swab. The eluates were then immediately transferred to lyophilized reactions already present on the instrument to initiate amplification and detection. Samples in UTM were screened by adding 200 µl of UTM into 2.5 ml of pre-heated elution/lysis buffer and mixing briefly (by pipetting up and down). The eluates were then immediately transferred to lyophilized reactions already present on the instrument to initiate amplification and detection. All clinical samples were thawed and allowed to reach ambient temperature prior to their use.

Ancillary testing on each sample was performed as follows: From each eluted/lysed swab eluate, 140 µl was used to purify RNA and DNA, respectively. These purified samples were subsequently used for RSV AB qPCR and human gDNA analysis. From each UTM sample, 140 µl was used directly (prior to elution/lysis) to purify RNA and DNA, respectively. The Qiagen QIAamp Viral RNA Mini Kit (catalog #52904) was used for nucleic acid purifications. RNase/DNase testing was performed using the IDT RNase Alert (cat #11-02-01-02) and DNase Alert (cat #11-02-01-04) kits. From each eluted/lysed swab eluate, 1 µl and a 1:10 dilution of 1 µl were screened in each nuclease test. From each UTM sample, 1 µl and a 1:10 dilution of 1 µl were screened in each nuclease test, prior to elution/lysis. Following clinical sample use, aliquots were frozen at −80° C.

The results from all tests described above are summarized in the following tables (Tables 6-7), and include the RSV NEAR call (+/− for RSV A and/or RSV B), the RSV A/B qPCR call (+/−) and RSV copy number, the human gDNA concentration (in nanograms) and the relative level of RNase/DNase activity for each sample. RSV A/B NEAR calls were made subjectively (fluorescence signal>=2× background was considered +) as an algorithm with defined cutoff thresholds was not developed at the time of clinical sample testing. FIGS. 26-33 depict summaries of the real time fluorescence curves for all clinical samples that were screened.

TABLE 6

RSV Clinical Sample Testing Summary—Direct Swab Data Summary

| | NEAR | | | | qPCR | | | Nucleases | | hu gDNA | |
| | | | | | Copy | | | | | human gDNA | human gDNA |
| | RSVA | RSVB | IC | NEAR RESULTS | qPCR RESULTS | # in NEAR | qPCR RSVA | qPCR RSVB | RNase | DNase | (Total in 2.5 mL) | in 100 uLs |
|---|---|---|---|---|---|---|---|---|---|---|---|---|
| 003A:002 | − | − | + | negative | − | | − | − | **** | 0.01-0.1 U | 1478 ng | 59 ng |
| 003A:004 | − | − | + | negative | − | | − | − | ** | − | 180 ng | 7 ng |
| 003A:007 | − | − | + | negative | − | | − | − | **** | − | 34172 ng | 1367 ng |
| 003A:009 | − | − | + | negative | − | | − | − | ** | − | 2027 ng | 81 ng |
| 003A:010 | − | − | + | negative | − | | − | − | *** | − | 22842 ng | 914 ng |
| 003A:012 | + | − | + | positive | positive | 497 copies | 58 copies | − | **** | − | 144 ng | 6 ng |
| 003A:016 | − | − | + | negative | − | | − | − | **** | − | 1224 ng | 49 ng |
| 003A:018 | − | + | + | positive | positive | 17 copies | − | 2 copies | * | − | 227 ng | 9 ng |
| 003A:020 | − | − | + | negative | − | | − | − | ** | − | 2472 ng | 99 ng |
| 003A:023 | − | − | + | negative | − | | − | − | * | − | 98 ng | 4 ng |
| 003A:025 | − | − | + | negative | − | | − | − | *** | − | 724 ng | 29 ng |
| 003A:028 | − | − | + | negative | − | | − | − | * | − | 51 ng | 2 ng |
| 003A:030 | − | − | + | negative | − | | − | − | *** | − | 6484 ng | 259 ng |
| 024A:001 | − | − | + | negative | − | | − | − | **** | <<0.01 U | 18736 ng | 749 ng |
| 024A:010 | + | + | + | positive | positive | 58,457 copies | − | 6,820 copies | ** | − | 885 ng | 35 ng |
| 024A:019 | − | − | + | negative | − | | − | − | **** | − | 1697 ng | 68 ng |
| 024A:028 | + | + | + | positive | positive | 1,528,774 copies | − | 178,357 copies | **** | − | 4417 ng | 177 ng |
| 024A:037 | + | + | + | positive | positive | 20,366 copies | − | 2,376 copies | *** | − | 201 ng | 8 ng |
| 024A:046 | − | + | + | positive | positive | 540 copies | − | 63 copies | *** | − | 3356 ng | 134 ng |
| 024A:055 | − | + | + | positive | positive | 15,926 copies | − | 1,858 copies | *** | − | 66 ng | 3 ng |
| 024A:064 | − | − | + | negative | − | | − | − | **** | − | 487 ng | 19 ng |
| 024A:073 | − | − | + | negative | − | | − | − | ** | − | 0 ng | 0 ng |
| 024A:082 | + | + | + | positive | positive | 484,551 copies | − | 56,531 copies | *** | − | 539 ng | 22 ng |
| 024A:091 | − | − | + | negative | − | | − | − | *** | − | 682 ng | 27 ng |
| 024A:109 | − | + | + | positive | positive | 5,803 copies | − | 677 copies | *** | − | 9667 ng | 387 ng |
| 024A:126 | − | − | + | negative | − | | − | − | **** | − | 3274 ng | 131 ng |
| 003A:005 | − | − | + | negative | − | | − | − | *** | − | 16500 ng | 660 ng |
| 003A:013 | − | − | + | negative | − | | − | − | ** | − | 230 ng | 9 ng |
| 003A:017 | − | − | + | negative | − | | − | − | ** | − | 305 ng | 12 ng |
| 003A:027 | − | − | + | negative | − | | − | − | *** | − | 1385 ng | 55 ng |
| 024A:004 | − | − | + | negative | − | | − | − | **** | − | 2175 ng | 87 ng |
| 024A:008 | − | − | + | negative | − | | − | − | *** | − | 130 ng | 5 ng |
| 024A:017 | + | + | + | positive | positive | 828,231 copies | − | 96,627 copies | **** | − | 1185 ng | 47 ng |
| 024A:020 | − | − | + | negative | − | | − | − | ** | − | 14785 ng | 591 ng |
| 024A:023 | − | − | + | negative | − | | − | − | ** | − | 900 ng | 36 ng |
| 024A:029 | + | + | + | positive | positive | 42,566 to 10,586 copies | − | 4,966 to 1,235 copies | * | − | 35 ng | 1 ng |
| 024A:033 | − | − | + | negative | − | | − | − | ** | − | 10 ng | 0 ng |
| 024A:039 | − | − | + | negative | − | | − | − | * | − | 325 ng | 13 ng |
| 024A:042 | − | + | − | positive | positive | 130,543 copies | − | 15,230 copies | **** | − | 27750 ng | 1110 ng |
| 024A:047 | − | + | + | positive | positive | 12,086 copies | − | 1,410 copies | *** | − | 1015 ng | 41 ng |
| 024A:048 | + | − | + | positive | positive | 686 copies | 80 copies | − | **** | − | 80 ng | 3 ng |
| 024A:051 | + | − | + | positive | positive | 357,986 copies | − | 41,765 copies | *** | − | 285 ng | 11 ng |
| 024A:060 | − | − | + | negative | − | | − | − | *** | − | 210 ng | 8 ng |
| 024A:072 | − | − | + | negative | − | | − | − | **** | − | 75 ng | 3 ng |
| 024A:080 | + | − | + | positive | positive | 359,109 copies | 41,896 copies | − | ** | − | 1845 ng | 74 ng |
| 024A:107 | − | − | + | negative | − | | − | − | * | − | 1835 ng | 73 ng |
| 024A:116 | − | − | + | negative | − | | − | − | *** | − | 8320 ng | 333 ng |
| 024A:119 | + | + | + | positive | positive | 37,594 copies | 4,386 copies | − | * | − | 35 ng | 1 ng |
| 024A:125 | − | − | + | negative | − | | − | − | * | − | 595 ng | 24 ng |
| 024A:128 | − | − | + | negative | − | | − | − | * | − | 245 ng | 10 ng |

TABLE 7

Data Summary

| | NEAR | | | NEAR RESULTS | qPCR RESULTS | qPCR Copy # in NEAR | qPCR RSVA | qPCR RSVB | Nucleases | | hu gDNA human gDNA (Total in 2.5 mL) | human gDNA in 100 uLs |
|---|---|---|---|---|---|---|---|---|---|---|---|---|
| | RSVA | RSVB | IC | | | | | | RNase | DNase | | |
| #001A:001 | − | − | + | negative | − | | − | − | **** | − | 40000 ng | 1600 ng |
| #001A:009 | − | − | + | negative | − | | − | − | ** | <<0.01 U | 55 ng | 2 ng |
| #001A:017 | − | − | + | negative | − | | − | − | **** | <0.01 U | 150 ng | 6 ng |
| #001A:022 | − | − | + | negative | − | | − | − | **** | − | 17990 ng | 720 ng |
| #001A:029 | − | + | + | positive | positive | 31,824 copies | − | 50,123 copies | **** | − | 17005 ng | 680 ng |
| #001A:035 | − | + | + | positive | positive | 53,488 copies | − | 84,244 copies | **** | − | 16305 ng | 652 ng |
| #001A:042 | + | − | + | positive | positive | 139,378 copies | 219,520 copies | − | **** | − | 31770 ng | 1271 ng |
| #001A:053 | − | + | + | positive | positive | 4,646 copies | − | 7,317 copies | *** | − | 2110 ng | 84 ng |
| #001A:065 | − | − | + | negative | − | | − | − | **** | − | 25200 ng | 1008 ng |
| #001A:077 | − | − | + | negative | − | | − | − | *** | − | 1415 ng | 57 ng |
| #001A:086 | − | + | + | positive | positive | 211,438 copies | − | 333,015 copies | **** | − | 7120 ng | 285 ng |
| #001A:094 | − | − | + | negative | − | | − | − | **** | − | 3455 ng | 138 ng |
| #001A:110 | − | − | + | negative | − | | − | − | *** | − | 3455 ng | 138 ng |
| #025A:002 | − | − | + | negative | − | | − | − | *** | − | 840 ng | 34 ng |
| #025A:007 | + | + | + | positive | positive | 1,394 copies | − | 2,196 copies | **** | − | 1810 ng | 72 ng |
| #025A:013 | + | + | L.P. | positive | positive | 141,282 copies | − | 222,519 copies | **** | − | 7220 ng | 289 ng |
| #025A:018 | − | − | + | negative | − | | − | − | | − | 25375 ng | 1015 ng |
| #025A:023 | − | + | − | positive | positive | 201,354 copies | − | 317,132 copies | **** | − | 28795 ng | 1152 ng |
| #025A:029 | − | − | + | negative | − | | − | − | **** | − | 18245 ng | 730 ng |
| #025A:034 | − | + | + | positive | positive | 3,260 copies | − | 5,134 copies | *** | − | 14370 ng | 575 ng |
| #025A:036 | − | + | − | positive | positive | 399,122 copies | − | 628,601 copies | **** | − | 25555 ng | 1022 ng |
| #025A:044 | − | − | + | negative | − | | − | − | **** | − | 20700 ng | 828 ng |
| #025A:051 | − | − | + | negative | − | | − | − | *** | − | 3290 ng | 132 ng |
| #025A:066 | − | − | + | negative | − | | − | − | *** | − | 15850 ng | 634 ng |
| #025A:067 | − | − | + | negative | − | | − | − | **** | − | 31325 ng | 1253 ng |
| #025A:069 | − | − | + | negative | − | | − | − | **** | − | 11000 ng | 440 ng |
| #001A:006 | − | − | + | negative | − | | − | − | **** | − | 7875 ng | 315 ng |
| #001A:007 | − | − | + | negative | − | | − | − | **** | − | 1150 ng | 46 ng |
| #001A:015 | + | + | + | positive | positive | 239,815 copies | 377,708 copies | − | **** | − | 915 ng | 37 ng |
| #001A:018 | − | − | + | negative | − | | − | − | − | <0.01 U | 0 ng | 0 ng |
| #001A:027 | + | + | + | positive | positive | 305,136 copies | 480,589 copies | − | **** | − | 7130 ng | 285 ng |
| #001A:030 | − | − | + | negative | − | | − | − | **** | − | 3480 ng | 139 ng |
| #001A:034 | + | − | + | positive | positive | 115,543 copies | 181,981 copies | − | **** | − | 17065 ng | 683 ng |
| #001A:037 | + | − | + | positive | positive | 38,769 copies | 61,061 copies | − | **** | − | 7335 ng | 293 ng |
| #001A:054 | − | − | + | negative | − | | − | − | **** | − | 56625 ng | 2265 ng |
| #001A:057 | + | − | + | positive | positive | 45,474 copies | 71,621 copies | − | **** | − | 1905 ng | 76 ng |
| #001A:062 | − | − | + | negative | − | | − | − | ** | − | 0 ng | 0 ng |
| #001A:068 | − | + | + | positive | positive | 418,119 copies | 658,537 copies | − | **** | − | 6830 ng | 273 ng |
| #001A:075 | − | + | + | positive | positive | 98,537 copies | − | 155,195 copies | **** | − | 245 ng | 10 ng |
| #001A:085 | − | − | + | negative | − | | − | − | **** | − | 180 ng | 7 ng |
| #001A:092 | − | − | + | negative | − | | − | − | *** | − | 370 ng | 15 ng |
| #025A:005 | − | + | + | positive | positive | 98,537 copies | − | 155,195 copies | **** | − | 13990 ng | 560 ng |
| #025A:008 | − | − | + | negative | positive | 3 copies (Below LOD) | − | 5 copies | **** | − | 15125 ng | 605 ng |
| #025A:016 | + | + | + | positive | positive | 95,540 copies | − | 150,476 copies | **** | − | 14700 ng | 588 ng |
| #025A:021 | − | − | + | negative | − | | − | − | **** | − | 25035 ng | 1001 ng |
| #025A:027 | + | − | + | positive | positive | 46,603 copies | 73,400 copies | − | **** | − | 55430 ng | 2217 ng |
| #025A:037 | − | − | + | negative | − | | − | − | **** | − | 3360 ng | 134 ng |
| #025A:048 | − | − | + | negative | − | | − | − | **** | − | 29685 ng | 1187 ng |

TABLE 7-continued

Data Summary

| | NEAR | | | qPCR | | | | hu gDNA | |
| | | | | | Copy | | | Nucleases | human gDNA (Total in 2.5 mL) | human gDNA in 100 uLs |
| | RSVA | RSVB | IC | NEAR RESULTS | qPCR RESULTS | # in NEAR | qPCR RSVA | qPCR RSVB | RNase | DNase | | |
|---|---|---|---|---|---|---|---|---|---|---|---|---|
| #025A:060 | − | − | + | negative | − | | − | − | **** | − | 40565 ng | 1623 ng |
| #025A:064 | − | − | + | negative | − | | − | − | **** | − | 6010 ng | 240 ng |

Note:
before sample ID indicate VTM sample

In more detail, of the 100 clinical samples screened to date, 38 were determined to be positive by qPCR (9 RSV A, 29 RSV B), with a wide range of titers, giving a prevalence of 38%. RSV A titers ranged from 497 copies/reaction to 1,881,600 copies/reaction. RSV B titers ranged from 26 copies/reaction to 5,388,009 copies/reaction. The RSV AB NEAR assays performed. The RSV A & B assays were able to detect all qPCR positive samples as NEAR positive except for the lowest RSV B sample (26 copies/reaction), which is below the assay's LOD. These results provided an overall sensitivity of 97.4%, and specificity of 100%. Further, there were no invalid calls, resulting in an invalid rate of 0%. As noted in Example 6, the RSV A & B NEAR assays are cross-reactive with one another, and this can be seen in the clinical sample testing. Of the 9 qPCR confirmed RSV A positive samples, 1 was detected as positive by the RSV B NEAR assay. Of the 29 qPCR confirmed RSV B positive samples, 12 were detected as positive by the RSV A NEAR assay.

With respect to the potentially inhibitory characteristics of the clinical samples that were screened, the amount of human gDNA present in each sample varied greatly, from as little as no detectable gDNA to 1.6 µg per 100 µl NEAR reaction (Table 8).

TABLE 8

Human gDNA content per 100 µl of clinical sample eluate
Clinical samples
Human gDNA per 100 µl

| gDNA (ng) | Count |
|---|---|
| 0-10 | 23 |
| 10-100 | 29 |
| 100-250 | 9 |
| 250-500 | 10 |
| 500-750 | 13 |
| 750-1000 | 2 |
| >1000 | 14 |
| Total | 100 |

The RNase activity also varied greatly, as measured using the qualitative RNase Alert assay. The level of RNase activity was subjectively segregated into four levels, high (4 stars), moderate (3 stars), low (2 stars) and very low (1 star). A call of high RNase activity was the result of saturating signal in the RNase Alert assay. A level of very low was the result of a signal slightly above the baseline level (negative control) of RNase activity in the RNase Alert assay (Table 9). Overall, the majority of clinical samples possessed large amounts of RNase activity, which could potentially lead to assay inhibition when the target is an RNA species, such as in the RSV test. Finally, of the 100 clinical samples tested, only 7 had measureable DNase activity, and all 7 samples possessed very low levels of DNase, suggesting that this potential inhibitor does not play a significant role in nasal swab inhibition of the RSV test.

TABLE 9

RNAse content per 100 µl of clinical sample eluate
Clinical samples
RNase Activity per 100 µl

| RNase | Count |
|---|---|
| High | 52 |
| Moderate | 24 |
| Low | 13 |
| Very low | 11 |
| Total | 100 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a forward template comprising a nucleic acid sequence comprising a recognition region at the 3' end that is complementary to the 3' end of a Respiratory Syncytial Virus (RSV) nonstructural NS2 gene antisense strand; a nicking enzyme binding site and a nicking site upstream of the recognition region; and a stabilizing region upstream of the nicking site, wherein the nucleic acid sequence of the forward template comprises a nucleotide sequence having at least 80%, at least 85%, or at least 95% sequence identity to SEQ ID NO: 1 (CGACTCACACGAGTCGAAAACTTGATGAAAGA); and a reverse template comprising a nucleic acid sequence comprising a recognition region at the 3' end that is complementary to the 3' end of a RSV nonstructural NS2 gene sense strand; a nicking enzyme binding site and a nicking site upstream of the recognition region; and a stabilizing region upstream of the nicking site, wherein the nucleic acid sequence of the reverse template comprises a nucleotide sequence having at least 80%, at least 85%, or at least 95% sequence identity to SEQ ID NO: 2 (AGACTCCACACGGAGTCTAGTTGACCAGGAATG).

2. The composition of claim 1, wherein the composition further comprises a probe oligonucleotide conjugated to a detectable label, wherein said probe oligonucleotide comprises a nucleotide sequence complementary to the RSV nonstructural NS2 gene nucleotide sequence.

3. The composition of claim 2, wherein the detectable label of the probe oligonucleotide is selected from the group consisting of a fluorophore, an enzyme, a quencher, an enzyme inhibitor, a radioactive label, a member of a binding pair and any combination thereof.

4. The composition of claim 1, wherein the composition further comprises a probe oligonucleotide comprising a nucleotide sequence having at least 80%, at least 85%, or at least 95% sequence identity to SEQ ID NO: 3 (ACCAGGAATGTAAATGTGGCCTGGT).

5. The composition of claim 1, further comprising one or more of a DNA polymerase, one or more nicking enzymes, dNTPs, or a mixture of dNTPs and ddNTPs.

6. The composition of claim 5, wherein the DNA polymerase is selected from the group consisting of Geobacillus bogazici DNA polymerase, Bst (large fragment), exo-DNA Polymerase, and Manta 1.0 DNA Polymerase.

7. The composition of claim 5, wherein the one or more nicking enzymes is/are independently selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, Nt.Bpu10I, and N.BspD6I.

8. The composition of claim 1, wherein the forward template and/or the reverse template comprises one or more modified nucleotides, spacers, or blocking groups.

9. A kit comprising:
a pair of template oligonucleotides selected from the group consisting of:
(a) a first pair of template oligonucleotides comprising a first forward template comprising a nucleotide sequence having at least 80%, at least 85%, or at least 95% sequence identity to SEQ ID NO: 1; and
a first reverse template comprising a nucleotide sequence having at least 80%, at least 85%, or at least 95% sequence identity to SEQ ID NO 2; and
(b) a second pair of template oligonucleotides comprising a second forward template comprising a nucleotide sequence having at least 80%, at least 85%, or at least 95% sequence identity to SEQ ID NO: 6; and a second reverse template comprising a nucleotide sequence having at least 80%, at least 85%, or at least 95% sequence identity to SEQ ID NO: 7.

10. A composition comprising a forward template comprising a nucleic acid sequence comprising a recognition region at the 3' end that is complementary to the 3' end of a RSV nucleocapsid gene N antisense strand; a nicking enzyme binding site and a nicking site upstream of the recognition region;

and a stabilizing region upstream of the nicking site, wherein the nucleic acid sequence of the forward template comprises a nucleotide sequence having at least 80%, at least 85%, or at least 95% sequence identity to SEQ ID NO: 6 (GACTCGCACACGAGT-CACGTAGTACAGGAGATAA); and a reverse template comprising a nucleic acid sequence comprising a recognition region at the 3' end that is complementary to the 3' end of a RSV nucleocapsid gene N sense strand; a nicking enzyme binding site and a nicking site upstream of the recognition region; and a stabilizing region upstream of the nicking site, wherein the nucleic acid sequence of the reverse template comprises a nucleotide sequence having at least 80%, at least 85%, or at least 95% sequence identity to SEQ ID NO: 7: (GACTCCACACG-GAGTCGCTTTTGCACATCATAA).

11. The composition of claim 10, wherein the composition further comprises a probe oligonucleotide conjugated to a detectable label, wherein said probe oligonucleotide comprises a nucleotide sequence complementary to the RSV nucleocapsid gene N nucleotide sequence.

12. The composition of claim 11, wherein the detectable label of the probe oligonucleotide is selected from the group consisting of a fluorophore, an enzyme, a quencher, an enzyme inhibitor, a radioactive label, a member of a binding pair and any combination thereof.

13. The composition of claim 10, wherein the composition further comprises a probe oligonucleotide comprising a nucleotide sequence having at least 80%, at least 85%, or at least 95% sequence identity to SEQ ID NO: 8 (TGACA-CATCATAATTGGGAGTGTCA).

14. The composition of claim 10, further comprising one or more of a DNA polymerase, one or more nicking enzymes, dNTPs, or a mixture of dNTPs and ddNTPs.

15. The composition of claim 14, wherein the DNA polymerase is selected from the group consisting of *Geobacillus bogazici* DNA polymerase, Bst (large fragment), exo-DNA Polymerase, and Manta 1.0 DNA Polymerase.

16. The composition of claim 14, wherein the one or more nicking enzymes is/are independently selected from the group consisting of Nt.BspQI, Nb.BbvCi, Nb.Bsml, Nb.BsrDI, Nb.Btsl, Nt.Alwl, Nt.BbvCI, Nt.BstNBI, Nt.Cvi-PII, Nb.Bpu10l, Nt.Bpu10l, and N.BspD61.

17. The composition of claim 10, wherein the forward template and/or the reverse template comprises one or more modified nucleotides, spacers, or blocking groups.

* * * * *

UNITED STATES PATENT AND TRADEMARK OFFICE
CERTIFICATE OF CORRECTION

PATENT NO. : 11,634,770 B2
APPLICATION NO. : 16/118081
DATED : April 25, 2023
INVENTOR(S) : Honghua Zhang and Richard Roth It is certified that error appears in the above-identified patent and that said Letters Patent is hereby corrected as shown below:

In the Claims

Claim 6, Column 44, Line 44 reads:
"bogazici DNA polymerase, Bst (large fragment), exo-DNA"

Whereas it should read:
"*bogazici* DNA polymerase, Bst (large fragment), exo⁻ DNA"

And

Claim 5, Column 44, Lines 48-50 read:
"group consisting of Nt.BspQI, Nb.BbvCi, Nb.Bsml, Nb.BsrDI, Nb.Btsl, Nt.AlWl, Nt.BbvCI, Nt.BstNBI, Nt.Cvi-PII, Nb.Bpu10l, Nt.Bpu10l, and N.BspD61."

Whereas it should read:
"group consisting of Nt.BspQI, Nb.BbvCi, Nb.BsmI, Nb.BsrDI, Nb.BtsI, Nt.AlwI, Nt.BbvCI, Nt.BstNBI, Nt.Cvi-PII, Nb.Bpu10I, Nt.Bpu10I, and N.BspD61."

and

Claim 15, Column 46, Lines 18-19 read:
"*bacillus* bogazici DNA polymerase, Bst (large fragment), exo-DNA Polymerase, and Manta 1.0 DNA Polymerase."

Whereas it should read:
"*bacillus bogazici* DNA polymerase, Bst (large fragment), exo⁻ DNA Polymerase, and Manta 1.0 DNA Polymerase."

Signed and Sealed this
Thirteenth Day of June, 2023

Katherine Kelly Vidal
*Director of the United States Patent and Trademark Office*

CERTIFICATE OF CORRECTION (continued)
U.S. Pat. No. 11,634,770 B2

And

Claim 16, Column 46, Lines 22-24 read:
"group consisting of Nt.BspQI, Nb.BbvCi, Nb.Bsml,
Nb.BsrDI, Nb.Btsl, Nt.Alwl, Nt.BbvCI, Nt.BstNBI, Nt.Cvi-
PII, Nb.Bpu10l, Nt.Bpu10l, and N.BspD61."

Whereas it should read:
"group consisting of Nt.BspQI, Nb.BbvCi, Nb.BsmI,
Nb.BsrDI, Nb.BtsI, Nt.AlwI, Nt.BbvCI, Nt.BstNBI, Nt.Cvi-
PII, Nb.Bpu10I, Nt.Bpu10I, and N.BspD61."

SEQUENCE LISTING

<160> NUMBER OF SEQ ID NOS: 14

<210> SEQ ID NO 1
<211> LENGTH: 32
<212> TYPE: DNA
<213> ORGANISM: Respiratory syncytial virus

```
<400> SEQUENCE: 1
cgactcacac gagtcgaaaa cttgatgaaa ga                                    32

<210> SEQ ID NO 2
<211> LENGTH: 33
<212> TYPE: DNA
<213> ORGANISM: Respiratory syncytial virus

<400> SEQUENCE: 2
agactccaca cggagtctag ttgaccagga atg                                   33

<210> SEQ ID NO 3
<211> LENGTH: 25
<212> TYPE: DNA
<213> ORGANISM: Respiratory syncytial virus

<400> SEQUENCE: 3
accaggaatg taaatgtggc ctggt                                            25

<210> SEQ ID NO 4
<211> LENGTH: 38
<212> TYPE: DNA
<213> ORGANISM: Respiratory syncytial virus

<400> SEQUENCE: 4
acttgatgaa agacaggcca catttacatt cctggtca                              38

<210> SEQ ID NO 5
<211> LENGTH: 38
<212> TYPE: DNA
<213> ORGANISM: Respiratory syncytial virus

<400> SEQUENCE: 5
tgaccaggaa tgtaaatgtg gcctgtcttt catcaagt                              38

<210> SEQ ID NO 6
<211> LENGTH: 34
<212> TYPE: DNA
<213> ORGANISM: Human respiratory syncytial virus B strain N2

<400> SEQUENCE: 6
gactcgcaca cgagtcacgt agtacaggag ataa                                  34

<210> SEQ ID NO 7
<211> LENGTH: 33
<212> TYPE: DNA
<213> ORGANISM: Human respiratory syncytial virus B strain N2

<400> SEQUENCE: 7
gactccacac ggagtcgctt ttgcacatca taa                                   33

<210> SEQ ID NO 8
<211> LENGTH: 25
<212> TYPE: DNA
<213> ORGANISM: Human respiratory syncytial virus B strain N2
<220> FEATURE:
<221> NAME/KEY: misc_feature
<222> LOCATION: (14)..(14)
<223> OTHER INFORMATION: 2'-O-methyl modified nucleotide
<220> FEATURE:
<221> NAME/KEY: misc_feature
<222> LOCATION: (19)..(19)
<223> OTHER INFORMATION: 2'-O-methyl modified nucleotide
```

<400> SEQUENCE: 8
tgacacatca taattgggag tgtca                                      25

<210> SEQ ID NO 9
<211> LENGTH: 22
<212> TYPE: DNA
<213> ORGANISM: Human respiratory syncytial virus B strain N2

<400> SEQUENCE: 9
ccgtcaacca cacacctgac gg                                         22

<210> SEQ ID NO 10
<211> LENGTH: 46
<212> TYPE: RNA
<213> ORGANISM: Human respiratory syncytial virus B strain N2

<400> SEQUENCE: 10
auuugcacau cauaaccaca caccugacgu uaucuccugu acuaca                46

<210> SEQ ID NO 11
<211> LENGTH: 42
<212> TYPE: DNA
<213> ORGANISM: Human respiratory syncytial virus B strain N2

<400> SEQUENCE: 11
agtacaggag ataatattga cactcccaat tatgatgtgc aa                   42

<210> SEQ ID NO 12
<211> LENGTH: 42
<212> TYPE: DNA
<213> ORGANISM: Human respiratory syncytial virus B strain N2

<400> SEQUENCE: 12
ttgcacatca taattgggag tgtcaatatt atctcctgta ct                   42

<210> SEQ ID NO 13
<211> LENGTH: 41
<212> TYPE: DNA
<213> ORGANISM: Human respiratory syncytial virus B strain N2

<400> SEQUENCE: 13
agtacaggag ataacgtcag gtgtgtggtt atgatgtgca a                    41

<210> SEQ ID NO 14
<211> LENGTH: 879
<212> TYPE: DNA
<213> ORGANISM: Human respiratory syncytial virus B strain N2
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

```
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
```

-continued

```
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (806)..(806)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
```

<220> FEATURE:
<221> NAME/KEY: misc_feature
<222> LOCATION: (871)..(871)
<223> OTHER INFORMATION: n is a, c, g, or t

<400> SEQUENCE: 14

```
ttgcacatca taaccacaca cctgacgtta tctcctgtac tdsncsdncn dtnrsvatma        60
ttcgactcac acgagtcgaa aacttgatga aaganmrsva tmattmagac tccacacgga       120
gtctagttmg maccaggaat gnmrsvmcar bacnmbrmac caggaatgmt aaamtgtggm       180
cctggtnmrs vaacttgatg aaagacaggc cacatttaca ttcctggtca rsvatgacca       240
ggaatgtaaa tgtggcctgt ctttcatcaa gtmmthymdd nctdmrcdsm ddnctdndtn       300
mncatrbdsa crsncrtarg trdcttabrs vbassaydta sdsncsdncn dtnrsvbtma       360
ttgactcgca cacgagtcac gtagtacagg agataanmrs vbtmattgac tccacacgga       420
gtcgcttttg cacatcataa nmrsvbmcar bacnmbrmtg acacatcata amttgggmag       480
tgtcanmrsv bntrnacntr cmcarbacnm bamccgtcaa ccacacacct gacggnmrsv       540
bcagcacaca aaccacacac cgacgacccg acacakcsrs vbagtacagg agataatatt       600
gacactccca attatgatgt gcaarsvbtt gcacatcata attgggagtg tcaatattat       660
ctcctgtact rsvbcagtac aggagataac gtcaggtgtg tggttatgat gtgcaarsvb       720
cttgcacatc ataaccacac acctgacgtt atctcctgta ctmmthymdd nctdmrcdsm       780
ddnctdndtn mncatrhshr thatbndbds acrsncrtar gtrdctndrn dsacrsncrn       840
trnacntrcr dcttacssac rsncntrnac ntrctargt                             879
```